US012773181B2

(12) United States Patent
Prince

(10) Patent No.: US 12,773,181 B2
(45) Date of Patent: *Oct. 27, 2026

(54) AUTOMATIC VESSEL DETECTION TOOLS AND METHODS

(71) Applicant: Bard Access Systems, Inc., Salt Lake City, UT (US)

(72) Inventor: Matthew J. Prince, Herriman, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/936,351

(22) Filed: Nov. 4, 2024

(65) Prior Publication Data

US 2025/0057501 A1 Feb. 20, 2025

Related U.S. Application Data

(63) Continuation of application No. 18/238,281, filed on Aug. 25, 2023, now Pat. No. 12,138,108, which is a (Continued)

(51) Int. Cl.

*A61B 8/06* (2006.01)
*A61B 8/00* (2006.01)

(Continued)

(52) U.S. Cl.

CPC .................. *A61B 8/06* (2013.01); *A61B 8/02* (2013.01); *A61B 8/463* (2013.01); *A61B 8/465* (2013.01);

(Continued)

(58) Field of Classification Search

CPC .............................. A61B 8/085; A61B 8/0891
See application file for complete search history.

(56) References Cited

U.S. PATENT DOCUMENTS 3,697,917 A 10/1972 Orth et al.
5,148,809 A 9/1992 Biegeleisen-Knight et al.

(Continued)

FOREIGN PATENT DOCUMENTS

CN 102871645 A 1/2013
CN 105107067 B 5/2018

(Continued)

OTHER PUBLICATIONS

EP 20866520.8 filed Apr. 5, 2022 Extended European Search Report dated Aug. 22, 2023.

(Continued)

*Primary Examiner* — Colin T. Sakamoto
*Assistant Examiner* — Tommy T Ly
(74) *Attorney, Agent, or Firm* — Rutan & Tucker LLP

(57) ABSTRACT

Disclosed herein is an ultrasound system for accessing a vasculature of a patient. The ultrasound system is configured to depict an enhanced ultrasound image of a subcutaneous portion of the patient including an icon surrounding a target vessel depicted on the display. The icon indicates to a clinician the target vessel is within range of a percentage vessel occupancy or vessel purchase length depending on a size of cannula or angle of insertion. The icon can also indicate blood flow strength, vessel type, or vessel deformation. The enhanced image can further include cannula trajectory guidelines and visual alerts for the clinician if the cannula tip can potentially backwall the vessel. Additional icons can indicate obstructions disposed on the cannula trajectory.

18 Claims, 10 Drawing Sheets

Related U.S. Application Data continuation of application No. 17/020,476, filed on Sep. 14, 2020, now Pat. No. 11,759,166.

(60) Provisional application No. 62/903,545, filed on Sep. 20, 2019.

(51) Int. Cl.
*A61B 8/02* (2006.01)
*A61B 17/34* (2006.01)

(52) U.S. Cl.
CPC .......... *A61B 8/488* (2013.01); *A61B 17/3403* (2013.01); *A61B 2017/3413* (2013.01)

(56) References Cited

U.S. PATENT DOCUMENTS

| | | | |
|---|---|---|---|
| 5,181,513 | A | 1/1993 | Touboul et al. |
| 5,325,293 | A | 6/1994 | Dorne |
| 5,349,865 | A | 9/1994 | Kavli et al. |
| 5,441,052 | A | 8/1995 | Miyajima |
| 5,549,554 | A | 8/1996 | Miraki |
| 5,573,529 | A | 11/1996 | Haak et al. |
| 5,758,650 | A | 6/1998 | Miller et al. |
| 5,775,322 | A | 7/1998 | Silverstein et al. |
| 5,879,297 | A | 3/1999 | Haynor et al. |
| 5,897,503 | A | 4/1999 | Lyon et al. |
| 5,908,387 | A | 6/1999 | LeFree et al. |
| 5,967,984 | A | 10/1999 | Chu et al. |
| 5,970,119 | A | 10/1999 | Hofmann |
| 6,004,270 | A | 12/1999 | Urbano et al. |
| 6,019,724 | A | 2/2000 | Gronningsaeter et al. |
| 6,068,599 | A | 5/2000 | Saito et al. |
| 6,074,367 | A | 6/2000 | Hubbell |
| 6,129,668 | A | 10/2000 | Haynor et al. |
| 6,132,379 | A | 10/2000 | Patacsil et al. |
| 6,216,028 | B1 | 4/2001 | Haynor et al. |
| 6,233,476 | B1 | 5/2001 | Strommer et al. |
| 6,245,018 | B1 | 6/2001 | Lee |
| 6,263,230 | B1 | 7/2001 | Haynor et al. |
| 6,375,615 | B1 | 4/2002 | Flaherty et al. |
| 6,436,043 | B2 | 8/2002 | Bonnefous |
| 6,498,942 | B1 | 12/2002 | Esenaliev et al. |
| 6,503,205 | B2 | 1/2003 | Manor et al. |
| 6,508,769 | B2 | 1/2003 | Bonnefous |
| 6,511,458 | B2 | 1/2003 | Milo et al. |
| 6,524,249 | B2 | 2/2003 | Moehring et al. |
| 6,543,642 | B1 | 4/2003 | Milliorn |
| 6,554,771 | B1 | 4/2003 | Buil et al. |
| 6,592,520 | B1 | 7/2003 | Peszynski et al. |
| 6,592,565 | B2 | 7/2003 | Twardowski |
| 6,601,705 | B2 | 8/2003 | Molina et al. |
| 6,612,992 | B1 | 9/2003 | Hossack et al. |
| 6,613,002 | B1 | 9/2003 | Clark et al. |
| 6,623,431 | B1 | 9/2003 | Sakuma et al. |
| 6,641,538 | B2 | 11/2003 | Nakaya et al. |
| 6,647,135 | B2 | 11/2003 | Bonnefous |
| 6,687,386 | B1 | 2/2004 | Ito et al. |
| 6,733,458 | B1 | 5/2004 | Steins et al. |
| 6,749,569 | B1 | 6/2004 | Pellegretti |
| 6,754,608 | B2 | 6/2004 | Svanerudh et al. |
| 6,755,789 | B2 | 6/2004 | Stringer et al. |
| 6,840,379 | B2 | 1/2005 | Franks-Farah et al. |
| 6,857,196 | B2 | 2/2005 | Dalrymple |
| 6,979,294 | B1 | 12/2005 | Selzer et al. |
| 7,074,187 | B2 | 7/2006 | Selzer et al. |
| 7,244,234 | B2 | 7/2007 | Ridley et al. |
| 7,359,554 | B2 | 4/2008 | Klingensmith et al. |
| 7,534,209 | B2 | 5/2009 | Abend et al. |
| 7,599,730 | B2 | 10/2009 | Hunter et al. |
| 7,637,870 | B2 | 12/2009 | Flaherty et al. |
| 7,681,579 | B2 | 3/2010 | Schwartz |
| 7,691,061 | B2 | 4/2010 | Hirota |
| 7,699,779 | B2 | 4/2010 | Sasaki et al. |
| 7,720,520 | B2 | 5/2010 | Willis |
| 7,727,153 | B2 | 6/2010 | Fritz et al. |
| 7,734,326 | B2 | 6/2010 | Pedain et al. |
| 7,831,449 | B2 | 11/2010 | Ying et al. |
| 7,905,837 | B2 | 3/2011 | Suzuki |
| 7,925,327 | B2 | 4/2011 | Weese |
| 7,927,278 | B2 | 4/2011 | Selzer et al. |
| 8,014,848 | B2 | 9/2011 | Birkenbach et al. |
| 8,038,619 | B2 | 10/2011 | Steinbacher |
| 8,060,181 | B2 | 11/2011 | Rodriguez Ponce et al. |
| 8,075,488 | B2 | 12/2011 | Burton |
| 8,090,427 | B2 | 1/2012 | Eck et al. |
| 8,105,239 | B2 | 1/2012 | Specht |
| 8,172,754 | B2 | 5/2012 | Watanabe et al. |
| 8,175,368 | B2 | 5/2012 | Sathyanarayana |
| 8,200,313 | B1 | 6/2012 | Rambod et al. |
| 8,211,023 | B2 | 7/2012 | Swan et al. |
| 8,228,347 | B2 | 7/2012 | Beasley et al. |
| 8,298,147 | B2 | 10/2012 | Huennekens et al. |
| 8,303,505 | B2 | 11/2012 | Webler et al. |
| 8,323,202 | B2 | 12/2012 | Roschak et al. |
| 8,328,727 | B2 | 12/2012 | Miele et al. |
| 8,336,536 | B1 | 12/2012 | Wood-Putnam et al. |
| 8,388,541 | B2 | 3/2013 | Messerly et al. |
| 8,409,103 | B2 | 4/2013 | Grunwald et al. |
| 8,449,465 | B2 | 5/2013 | Nair et al. |
| 8,553,954 | B2 | 10/2013 | Saikia |
| 8,556,815 | B2 | 10/2013 | Pelissier et al. |
| 8,585,600 | B2 | 11/2013 | Liu et al. |
| 8,622,913 | B2 | 1/2014 | Dentinger et al. |
| 8,706,457 | B2 | 4/2014 | Hart et al. |
| 8,727,988 | B2 | 5/2014 | Flaherty et al. |
| 8,734,357 | B2 | 5/2014 | Taylor |
| 8,744,211 | B2 | 6/2014 | Owen |
| 8,754,865 | B2 | 6/2014 | Merritt et al. |
| 8,764,663 | B2 | 7/2014 | Smok et al. |
| 8,781,194 | B2 | 7/2014 | Malek et al. |
| 8,781,555 | B2 | 7/2014 | Burnside et al. |
| 8,790,263 | B2 | 7/2014 | Randall et al. |
| 8,849,382 | B2 | 9/2014 | Cox et al. |
| 8,939,908 | B2 | 1/2015 | Suzuki et al. |
| 8,961,420 | B2 | 2/2015 | Zhang |
| 9,022,940 | B2 | 5/2015 | Meier |
| 9,087,147 | B1 | 7/2015 | Fonte |
| 9,138,290 | B2 | 9/2015 | Hadjicostis |
| 9,199,082 | B1 | 12/2015 | Yared et al. |
| 9,204,858 | B2 | 12/2015 | Pelissier et al. |
| 9,220,477 | B2 | 12/2015 | Urabe et al. |
| 9,295,447 | B2 | 3/2016 | Shah |
| 9,320,493 | B2 | 4/2016 | Visveshwara |
| 9,357,980 | B2 | 6/2016 | Toji et al. |
| 9,364,171 | B2 | 6/2016 | Harris et al. |
| 9,427,207 | B2 | 8/2016 | Sheldon et al. |
| 9,445,780 | B2 | 9/2016 | Hossack et al. |
| 9,456,766 | B2 | 10/2016 | Cox et al. |
| 9,456,804 | B2 | 10/2016 | Tamada |
| 9,468,413 | B2 | 10/2016 | Hall et al. |
| 9,492,097 | B2 | 11/2016 | Wilkes et al. |
| 9,521,961 | B2 | 12/2016 | Silverstein et al. |
| 9,554,716 | B2 | 1/2017 | Burnside et al. |
| 9,582,876 | B2 | 2/2017 | Specht |
| 9,610,061 | B2 | 4/2017 | Ebbini et al. |
| 9,636,031 | B2 | 5/2017 | Cox |
| 9,649,037 | B2 | 5/2017 | Lowe et al. |
| 9,649,048 | B2 | 5/2017 | Cox et al. |
| 9,702,969 | B2 | 7/2017 | Hope Simpson et al. |
| 9,715,757 | B2 | 7/2017 | Ng et al. |
| 9,717,415 | B2 | 8/2017 | Cohen et al. |
| 9,731,066 | B2 | 8/2017 | Liu et al. |
| 9,814,433 | B2 | 11/2017 | Benishti et al. |
| 9,814,531 | B2 | 11/2017 | Yagi et al. |
| 9,861,337 | B2 | 1/2018 | Patwardhan et al. |
| 9,895,138 | B2 | 2/2018 | Sasaki |
| 9,913,605 | B2 | 3/2018 | Harris et al. |
| 9,949,720 | B2 | 4/2018 | Southard et al. |
| 10,043,272 | B2 | 8/2018 | Forzoni et al. |
| 10,449,330 | B2 | 10/2019 | Newman et al. |
| 10,524,691 | B2 | 1/2020 | Newman et al. |
| 10,751,509 | B2 | 8/2020 | Misener |
| 11,564,861 | B1 | 1/2023 | Gaines |

(56) References Cited

U.S. PATENT DOCUMENTS 11,844,656 B2 12/2023 Urabe et al.
11,900,593 B2 2/2024 Dhatt et al.
12,082,976 B2 9/2024 Urabe et al.
2002/0038088 A1 3/2002 Imran et al.
2003/0047126 A1 3/2003 Tomaschko
2003/0106825 A1 6/2003 Molina et al.
2003/0109910 A1 6/2003 Lachenbruch et al.
2003/0120154 A1 6/2003 Sauer et al.
2003/0125629 A1 7/2003 Ustuner
2003/0135115 A1 7/2003 Burdette et al.
2003/0149366 A1 8/2003 Stringer et al.
2003/0167030 A1 9/2003 Weitzel et al.
2003/0216648 A1 11/2003 Lizzi et al.
2004/0015080 A1 1/2004 Kelly et al.
2004/0055925 A1 3/2004 Franks-Farah et al.
2004/0197267 A1 10/2004 Black et al.
2005/0000975 A1 1/2005 Carco et al.
2005/0049504 A1 3/2005 Lo et al.
2005/0075597 A1 4/2005 Vournakis et al.
2005/0165299 A1 7/2005 Kressy et al.
2005/0251030 A1 11/2005 Azar et al.
2005/0267365 A1 12/2005 Sokulin et al.
2006/0004290 A1 1/2006 Smith et al.
2006/0013523 A1 1/2006 Childlers et al.
2006/0015039 A1 1/2006 Cassidy et al.
2006/0020204 A1 1/2006 Serra et al.
2006/0047617 A1 3/2006 Bacioiu et al.
2006/0079781 A1 4/2006 Germond-Rouet et al.
2006/0184029 A1 8/2006 Haim et al.
2006/0210130 A1 9/2006 Germond-Rouet et al.
2006/0241463 A1 10/2006 Shau et al.
2007/0043341 A1 2/2007 Anderson et al.
2007/0049822 A1 3/2007 Bunce et al.
2007/0073155 A1 3/2007 Park et al.
2007/0167738 A1 7/2007 Timinger et al.
2007/0199848 A1 8/2007 Ellswood et al.
2007/0239005 A1 10/2007 Ogasawara
2007/0239120 A1 10/2007 Brock et al.
2007/0249911 A1 10/2007 Simon
2007/0287886 A1 12/2007 Saadat
2008/0021322 A1 1/2008 Stone et al.
2008/0033293 A1 2/2008 Beasley et al.
2008/0033759 A1 2/2008 Finlay
2008/0051657 A1 2/2008 Rold
2008/0108930 A1 5/2008 Weitzel et al.
2008/0125651 A1* 5/2008 Watanabe ............ A61B 5/1075
600/437
2008/0146915 A1 6/2008 McMorrow
2008/0177186 A1 7/2008 Slater et al.
2008/0221425 A1 9/2008 Olson et al.
2008/0269605 A1 10/2008 Nakaya
2008/0294037 A1 11/2008 Richter
2008/0300491 A1 12/2008 Bonde et al.
2009/0012399 A1 1/2009 Sunagawa et al.
2009/0012401 A1 1/2009 Steinbacher
2009/0074280 A1 3/2009 Lu et al.
2009/0105594 A1 4/2009 Reynolds et al.
2009/0118612 A1 5/2009 Grunwald et al.
2009/0124903 A1 5/2009 Osaka
2009/0137887 A1 5/2009 Shariati et al.
2009/0137907 A1 5/2009 Takimoto et al.
2009/0143672 A1 6/2009 Harms et al.
2009/0143684 A1 6/2009 Cermak et al.
2009/0156926 A1 6/2009 Messerly et al.
2009/0171205 A1 7/2009 Kharin et al.
2009/0281413 A1 11/2009 Boyden et al.
2009/0306509 A1 12/2009 Pedersen et al.
2010/0010348 A1 1/2010 Halmann
2010/0168576 A1 7/2010 Poland et al.
2010/0211026 A2 8/2010 Sheetz et al.
2010/0249598 A1 9/2010 Smith et al.
2010/0286515 A1 11/2010 Gravenstein et al.
2010/0298705 A1* 11/2010 Pelissier .............. A61B 8/4254
600/443
2010/0312121 A1 12/2010 Guan
2010/0324423 A1 12/2010 El-Aklouk et al.
2011/0002518 A1 1/2011 Ziv-Ari et al.
2011/0026796 A1 2/2011 Hyun et al.
2011/0071404 A1 3/2011 Schmitt et al.
2011/0074244 A1 3/2011 Osawa
2011/0087107 A1 4/2011 Lindekugel et al.
2011/0137173 A1* 6/2011 Lowe ................... A61B 8/4483
600/454
2011/0166451 A1 7/2011 Blaivas et al.
2011/0282188 A1 11/2011 Burnside et al.
2011/0295108 A1 12/2011 Cox et al.
2011/0313293 A1 12/2011 Lindekugel et al.
2012/0136242 A1 5/2012 Qi et al.
2012/0136256 A1 5/2012 Nozaki et al.
2012/0143029 A1 6/2012 Silverstein et al.
2012/0165679 A1 6/2012 Orome et al.
2012/0179038 A1* 7/2012 Meurer .................. A61B 8/463
600/443
2012/0179042 A1 7/2012 Fukumoto et al.
2012/0179044 A1 7/2012 Chiang et al.
2012/0197132 A1 8/2012 O'Connor
2012/0220865 A1 8/2012 Brown et al.
2012/0277576 A1 11/2012 Lui
2013/0006111 A1 1/2013 Sasaki
2013/0006130 A1 1/2013 Olde et al.
2013/0041250 A1* 2/2013 Pelissier ................ A61B 8/461
600/424
2013/0102889 A1 4/2013 Southard et al.
2013/0131499 A1 5/2013 Chan et al.
2013/0131502 A1 5/2013 Blaivas et al.
2013/0144166 A1 6/2013 Specht et al.
2013/0150724 A1 6/2013 Blaivas et al.
2013/0188832 A1 7/2013 Ma et al.
2013/0197367 A1* 8/2013 Smok ..................... A61B 8/085
600/454
2013/0218024 A1 8/2013 Boctor et al.
2013/0323700 A1 12/2013 Samosky et al.
2013/0338503 A1 12/2013 Cohen et al.
2013/0338508 A1 12/2013 Nakamura et al.
2013/0345566 A1 12/2013 Weitzel et al.
2014/0005530 A1 1/2014 Liu et al.
2014/0031694 A1 1/2014 Solek
2014/0066779 A1 3/2014 Nakanishi
2014/0073976 A1 3/2014 Fonte et al.
2014/0100440 A1 4/2014 Cheline et al.
2014/0114194 A1 4/2014 Kanayama et al.
2014/0170620 A1 6/2014 Savitsky et al.
2014/0180098 A1 6/2014 Flaherty et al.
2014/0180116 A1 6/2014 Lindekugel et al.
2014/0188133 A1 7/2014 Misener
2014/0188440 A1 7/2014 Donhowe et al.
2014/0243671 A1 8/2014 Holl et al.
2014/0276048 A1 9/2014 Kiley et al.
2014/0276059 A1 9/2014 Sheehan
2014/0276069 A1 9/2014 Amble et al.
2014/0276081 A1 9/2014 Tegels
2014/0276085 A1 9/2014 Miller
2014/0276690 A1 9/2014 Grace
2014/0296694 A1 10/2014 Jaworski
2014/0343431 A1 11/2014 Vajinepalli et al.
2014/0357994 A1 12/2014 Jin et al.
2015/0005738 A1 1/2015 Blacker
2015/0011887 A1 1/2015 Ahn et al.
2015/0011900 A1 1/2015 Lu et al.
2015/0065916 A1 3/2015 Maguire et al.
2015/0073279 A1 3/2015 Cai et al.
2015/0080740 A1 3/2015 Hao et al.
2015/0112200 A1 4/2015 Oberg et al.
2015/0141821 A1 5/2015 Yoshikawa et al.
2015/0190111 A1 7/2015 Fry
2015/0209003 A1 7/2015 Halmann et al.
2015/0209113 A1 7/2015 Burkholz et al.
2015/0209510 A1 7/2015 Burkholz et al.
2015/0209526 A1 7/2015 Matsubara et al.
2015/0245820 A1 9/2015 Tamada
2015/0257735 A1 9/2015 Ball et al.
2015/0272448 A1 10/2015 Fonte et al.
2015/0282890 A1 10/2015 Cohen et al.
2015/0294497 A1 10/2015 Ng et al.

(56) References Cited

U.S. PATENT DOCUMENTS

| | | | |
|---|---|---|---|
| 2015/0297097 | A1 | 10/2015 | Matsubara et al. |
| 2015/0342572 | A1 | 12/2015 | Tahmasebi Maraghoosh et al. |
| 2015/0351675 | A1 | 12/2015 | Cheng |
| 2015/0359520 | A1 | 12/2015 | Shan et al. |
| 2015/0359991 | A1 | 12/2015 | Dunbar et al. |
| 2016/0000367 | A1 | 1/2016 | Lyon |
| 2016/0000399 | A1 | 1/2016 | Halmann et al. |
| 2016/0026894 | A1 | 1/2016 | Nagase |
| 2016/0029995 | A1 | 2/2016 | Navratil et al. |
| 2016/0038119 | A1 | 2/2016 | Desjardins |
| 2016/0081674 | A1 | 3/2016 | Bagwan et al. |
| 2016/0113517 | A1 | 4/2016 | Lee et al. |
| 2016/0113699 | A1 | 4/2016 | Sverdlik et al. |
| 2016/0120607 | A1 | 5/2016 | Sorotzkin et al. |
| 2016/0125639 | A1 | 5/2016 | Park et al. |
| 2016/0157831 | A1 | 6/2016 | Kang et al. |
| 2016/0166232 | A1 | 6/2016 | Merritt |
| 2016/0202053 | A1 | 7/2016 | Walker et al. |
| 2016/0211045 | A1 | 7/2016 | Jeon et al. |
| 2016/0213398 | A1 | 7/2016 | Liu |
| 2016/0220124 | A1 | 8/2016 | Grady et al. |
| 2016/0259992 | A1 | 9/2016 | Knodt et al. |
| 2016/0278869 | A1 | 9/2016 | Grunwald |
| 2016/0287214 | A1 | 10/2016 | Ralovich et al. |
| 2016/0296208 | A1 | 10/2016 | Sethuraman et al. |
| 2016/0374644 | A1 | 12/2016 | Mauldin, Jr. et al. |
| 2017/0014105 | A1 | 1/2017 | Chono |
| 2017/0020561 | A1 | 1/2017 | Cox et al. |
| 2017/0079548 | A1 | 3/2017 | Silverstein et al. |
| 2017/0086785 | A1 | 3/2017 | Bjaerum |
| 2017/0090571 | A1 | 3/2017 | Bjaerum et al. |
| 2017/0103534 | A1 | 4/2017 | Park et al. |
| 2017/0143312 | A1 | 5/2017 | Hedlund et al. |
| 2017/0157339 | A1 | 6/2017 | Li et al. |
| 2017/0164923 | A1 | 6/2017 | Matsumoto |
| 2017/0172666 | A1 | 6/2017 | Govari et al. |
| 2017/0196591 | A1 | 7/2017 | Long et al. |
| 2017/0215842 | A1* | 8/2017 | Ryu .................... A61B 8/4245 |
| 2017/0231553 | A1 | 8/2017 | Igarashi et al. |
| 2017/0252004 | A1 | 9/2017 | Broad et al. |
| 2017/0258522 | A1 | 9/2017 | Goshgarian et al. |
| 2017/0259013 | A1 | 9/2017 | Boyden et al. |
| 2017/0262982 | A1 | 9/2017 | Pagoulatos et al. |
| 2017/0290568 | A1 | 10/2017 | Ko et al. |
| 2017/0328751 | A1 | 11/2017 | Lemke |
| 2017/0367678 | A1 | 12/2017 | Sirtori et al. |
| 2018/0015256 | A1* | 1/2018 | Southard .............. A61B 8/0841 |
| 2018/0028110 | A1 | 2/2018 | Goldman et al. |
| 2018/0116723 | A1 | 5/2018 | Hettrick et al. |
| 2018/0125450 | A1 | 5/2018 | Blackbourne et al. |
| 2018/0161502 | A1 | 6/2018 | Nanan et al. |
| 2018/0199914 | A1 | 7/2018 | Ramachandran et al. |
| 2018/0214119 | A1 | 8/2018 | Mehrmohammadi et al. |
| 2018/0228465 | A1* | 8/2018 | Southard .............. A61B 8/4427 |
| 2018/0235649 | A1* | 8/2018 | Elkadi ................ A61B 18/1445 |
| 2018/0235709 | A1 | 8/2018 | Donhowe et al. |
| 2018/0289927 | A1 | 10/2018 | Messerly |
| 2018/0296185 | A1 | 10/2018 | Cox et al. |
| 2018/0310955 | A1 | 11/2018 | Lindekugel et al. |
| 2018/0333135 | A1 | 11/2018 | Kim et al. |
| 2018/0344293 | A1* | 12/2018 | Raju ...................... A61B 8/085 |
| 2019/0029636 | A1 | 1/2019 | Lee et al. |
| 2019/0060001 | A1 | 2/2019 | Kohli et al. |
| 2019/0060014 | A1 | 2/2019 | Hazelton et al. |
| 2019/0090855 | A1 | 3/2019 | Kobayashi et al. |
| 2019/0125210 | A1 | 5/2019 | Govari et al. |
| 2019/0200951 | A1 | 7/2019 | Meier |
| 2019/0239848 | A1* | 8/2019 | Bedi .................... A61B 5/7455 |
| 2019/0239850 | A1 | 8/2019 | Dalvin et al. |
| 2019/0307419 | A1 | 10/2019 | Durfee |
| 2019/0307515 | A1 | 10/2019 | Naito et al. |
| 2019/0307516 | A1 | 10/2019 | Schotzko et al. |
| 2019/0365347 | A1 | 12/2019 | Abe |
| 2019/0365348 | A1 | 12/2019 | Toume et al. |
| 2019/0365354 | A1 | 12/2019 | Du |
| 2019/0380676 | A1 | 12/2019 | Swan et al. |
| 2020/0027210 | A1 | 1/2020 | Haemel et al. |
| 2020/0069929 | A1* | 3/2020 | Mason ................ A61M 1/3656 |
| 2020/0085381 | A1 | 3/2020 | Weine et al. |
| 2020/0107596 | A1 | 4/2020 | Caruso et al. |
| 2020/0113540 | A1 | 4/2020 | Gijsbers et al. |
| 2020/0163654 | A1 | 5/2020 | Satir et al. |
| 2020/0200900 | A1 | 6/2020 | Asami et al. |
| 2020/0229795 | A1 | 7/2020 | Tadross et al. |
| 2020/0230391 | A1 | 7/2020 | Burkholz et al. |
| 2020/0237403 | A1 | 7/2020 | Southard et al. |
| 2020/0238403 | A1 | 7/2020 | Ahn et al. |
| 2020/0281561 | A1 | 9/2020 | Muller et al. |
| 2020/0281563 | A1 | 9/2020 | Muller et al. |
| 2020/0359990 | A1 | 11/2020 | Poland et al. |
| 2020/0390416 | A1 | 12/2020 | Swan et al. |
| 2021/0045716 | A1 | 2/2021 | Shiran et al. |
| 2021/0045967 | A1 | 2/2021 | Lampe et al. |
| 2021/0059639 | A1 | 3/2021 | Howell |
| 2021/0077058 | A1 | 3/2021 | Mashood et al. |
| 2021/0093383 | A1 | 4/2021 | Wang et al. |
| 2021/0137492 | A1 | 5/2021 | Imai |
| 2021/0146167 | A1 | 5/2021 | Barthe et al. |
| 2021/0161510 | A1 | 6/2021 | Sasaki et al. |
| 2021/0186467 | A1 | 6/2021 | Urabe et al. |
| 2021/0212658 | A1 | 7/2021 | McGrath et al. |
| 2021/0212668 | A1 | 7/2021 | Li et al. |
| 2021/0267569 | A1 | 9/2021 | Yamamoto |
| 2021/0267570 | A1 | 9/2021 | Ulman et al. |
| 2021/0295048 | A1 | 9/2021 | Buras et al. |
| 2021/0315538 | A1 | 10/2021 | Brandl et al. |
| 2021/0373602 | A1 | 12/2021 | Min |
| 2021/0378627 | A1 | 12/2021 | Yarmush et al. |
| 2022/0019313 | A1 | 1/2022 | He et al. |
| 2022/0022969 | A1 | 1/2022 | Misener |
| 2022/0039777 | A1 | 2/2022 | Durfee |
| 2022/0039829 | A1 | 2/2022 | Zijlstra et al. |
| 2022/0071593 | A1 | 3/2022 | Tran |
| 2022/0096053 | A1 | 3/2022 | Sethuraman et al. |
| 2022/0096797 | A1 | 3/2022 | Prince |
| 2022/0101980 | A1 | 3/2022 | Rothenberg et al. |
| 2022/0104791 | A1 | 4/2022 | Matsumoto |
| 2022/0104886 | A1 | 4/2022 | Blanchard et al. |
| 2022/0117582 | A1 | 4/2022 | McLaughlin et al. |
| 2022/0160434 | A1 | 5/2022 | Messerly et al. |
| 2022/0168050 | A1 | 6/2022 | Sowards et al. |
| 2022/0172354 | A1 | 6/2022 | Misener et al. |
| 2022/0225963 | A1 | 7/2022 | Sutton et al. |
| 2022/0233346 | A1 | 7/2022 | McElya |
| 2022/0296303 | A1 | 9/2022 | McLeod et al. |
| 2022/0304652 | A1 | 9/2022 | Peterson et al. |
| 2022/0330922 | A1 | 10/2022 | Sowards et al. |
| 2022/0334251 | A1 | 10/2022 | Sowards et al. |
| 2022/0338833 | A1 | 10/2022 | Dhatt et al. |
| 2022/0361840 | A1 | 11/2022 | Matsumoto et al. |
| 2022/0406460 | A1 | 12/2022 | Golan et al. |
| 2023/0044620 | A1 | 2/2023 | Shochat et al. |
| 2023/0048327 | A1 | 2/2023 | Lampe et al. |
| 2023/0107629 | A1 | 4/2023 | Sowards et al. |
| 2023/0113291 | A1 | 4/2023 | de Wild et al. |
| 2023/0132148 | A1 | 4/2023 | Sowards et al. |
| 2023/0135562 | A1 | 5/2023 | Misener et al. |
| 2023/0135757 | A1 | 5/2023 | Bauer et al. |
| 2023/0138970 | A1 | 5/2023 | Sowards et al. |
| 2023/0148872 | A1 | 5/2023 | Sowards et al. |
| 2023/0201539 | A1 | 6/2023 | Howell |
| 2023/0277153 | A1 | 9/2023 | Sowards et al. |
| 2023/0277154 | A1 | 9/2023 | Sowards et al. |
| 2023/0293143 | A1 | 9/2023 | Sowards et al. |
| 2023/0298757 | A1 | 9/2023 | Golan et al. |
| 2023/0338010 | A1 | 10/2023 | Sturm |
| 2023/0371928 | A1 | 11/2023 | Rajguru et al. |
| 2023/0381472 | A1 | 11/2023 | Chisena et al. |
| 2023/0397900 | A1 | 12/2023 | Prince |
| 2024/0065673 | A1 | 2/2024 | Sowards et al. |
| 2024/0197403 | A1 | 6/2024 | Mino et al. |
| 2024/0225597 | A1 | 7/2024 | Valois et al. |
| 2024/0307024 | A1 | 9/2024 | Sowards et al. |
| 2025/0017559 | A1 | 1/2025 | Denny et al. |

(56) References Cited

U.S. PATENT DOCUMENTS

| | | | |
|---|---|---|---|
| 2025/0104238 A1 | 3/2025 | Misener et al. |
| 2025/0177060 A1 | 6/2025 | Messerly et al. |
| 2025/0186026 A1 | 6/2025 | Tran |
| 2025/0251511 A1 | 8/2025 | Sowards et al. |
| 2025/0352167 A1 | 11/2025 | Sowards et al. |
| 2026/0123906 A1 | 5/2026 | Sowards et al. |

FOREIGN PATENT DOCUMENTS

| | | | |
|---|---|---|---|
| CN | 108778146 | A | 11/2018 |
| EP | 0933063 | A1 | 8/1999 |
| EP | 1504713 | A1 | 2/2005 |
| EP | 1591074 | B1 | 5/2008 |
| EP | 2823766 | A1 | 1/2015 |
| EP | 3181083 | A1 | 6/2017 |
| EP | 3870059 | | 9/2021 |
| FR | 3119752 | A1 | 8/2022 |
| JP | 2000271136 | A | 10/2000 |
| JP | 2007222291 | A | 9/2007 |
| JP | 2014150928 | A | 8/2014 |
| JP | 2018175547 | A | 11/2018 |
| KR | 20180070878 | A | 6/2018 |
| KR | 102176196 | B1 | 11/2020 |
| WO | 2004082749 | A2 | 9/2004 |
| WO | 2007115174 | A2 | 10/2007 |
| WO | 2010029521 | A2 | 3/2010 |
| WO | 2010076808 | A1 | 7/2010 |
| WO | 2013059714 | A1 | 4/2013 |
| WO | 2014115150 | A1 | 7/2014 |
| WO | 2015017270 | A1 | 2/2015 |
| WO | 2016081023 | A1 | 5/2016 |
| WO | 2017096487 | A1 | 6/2017 |
| WO | 2017214428 | A1 | 12/2017 |
| WO | 2018026878 | A1 | 2/2018 |
| WO | 2018134726 | A1 | 7/2018 |
| WO | 2018138343 | A1 | 8/2018 |
| WO | 2019232451 | A1 | 12/2019 |
| WO | 2020002620 | A1 | 1/2020 |
| WO | 2020016018 | A1 | 1/2020 |
| WO | 2019232454 | A9 | 2/2020 |
| WO | 2020044769 | A1 | 3/2020 |
| WO | 2020067897 | A1 | 4/2020 |
| WO | 2020083660 | A1 | 4/2020 |
| WO | 2020186198 | A1 | 9/2020 |
| WO | 2021123905 | A2 | 6/2021 |
| WO | 2021198226 | A1 | 10/2021 |
| WO | 2022069208 | A1 | 4/2022 |
| WO | 2022072727 | A2 | 4/2022 |
| WO | 2022081904 | A1 | 4/2022 |
| WO | 2022115479 | A1 | 6/2022 |
| WO | 2022119853 | A1 | 6/2022 |
| WO | 2022119856 | A1 | 6/2022 |
| WO | 2022221703 | A1 | 10/2022 |
| WO | 2022221714 | A1 | 10/2022 |
| WO | 2023059512 | A1 | 4/2023 |
| WO | 2023076268 | A1 | 5/2023 |
| WO | 2023081220 | A1 | 5/2023 |
| WO | 2023081223 | A1 | 5/2023 |
| WO | 2023091424 | A1 | 5/2023 |
| WO | 2023167866 | A1 | 9/2023 |
| WO | 2023177718 | A1 | 9/2023 |
| WO | 2024044277 | A1 | 2/2024 |
| WO | 2024180503 | A1 | 9/2024 |
| WO | 2025015198 | A1 | 1/2025 |

OTHER PUBLICATIONS

Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).

M. Ikhsan, K. K. Tan, AS. Putra, C. F. Kong, et. al., "Automatic identification of blood vessel cross-section for central venous catheter placement using a cascading classifier," 39th Annual International Conference of the IEEE Engineering in Medicine and Biology Society (EMBC). pp. 1489-1492 (Year: 2017).

Pagoulatos, N. et al. "New spatial localizer based on fiber optics with applications in 3D ultrasound imaging" Proceeding of Spie, vol. 3976 (Apr. 18, 2000; Apr. 18, 2020).

PCT/US2021/049294 filed Sep. 7, 2021 International Search Report and Written Opinion dated Dec. 8, 2021.

PCT/US2021/049712 filed Sep. 9, 2021 International Search Report and Written Opinion dated Dec. 14, 2021.

PCT/US2021/060622 filed Nov. 23, 2021 International Search Report and Written Opinion dated Mar. 3, 2022.

PCT/US2021/061267 filed Nov. 30, 2021 International Search Report and Written Opinion dated Mar. 9, 2022.

PCT/US2021/061276 filed Nov. 30, 2021 International Search Report and Written Opinion dated Mar. 9, 2022.

PCT/US2022/025082 filed Apr. 15, 2022 International Search Report and Written Opinion dated Jul. 11, 2022.

PCT/US2022/025097 filed Apr. 15, 2021 International Preliminary Report on Patentability dated Oct. 26, 2023.

PCT/US2022/025097 filed Apr. 15, 2022 International Search Report and Written Opinion dated Jul. 8, 2022.

PCT/US2022/045372 filed Sep. 30, 2022 International Search Report and Written Opinion dated Jan. 24, 2023.

PCT/US2022/048716 filed Nov. 2, 2022 International Search Report and Written Opinion dated Feb. 24, 2023.

PCT/US2022/048722 filed Nov. 2, 2022 International Search Report and Written Opinion dated Feb. 24, 2023.

PCT/US2022/049983 filed Nov. 15, 2022 International Search Report and Written Opinion dated Mar. 29, 2023.

PCT/US2022047727 filed Oct. 25, 2022 International Search Report and Written Opinion dated Jan. 25, 2023.

PCT/US2023/014143 filed Feb. 28, 2023 International Search Report and Written Opinion dated Jun. 12, 2023.

PCT/US2023/015266 filed Mar. 15, 2023 International Search Report and Written Opinion dated May 25, 2023.

PCT/US2023/030970 filed Aug. 23, 2023 International Search Report and Written Opinion dated Oct. 30, 2023.

PCT/US2024/037647 filed Jul. 11, 2024 International Search Report and Written Opinion dated Oct. 16, 2024.

Saxena Ashish et al Thermographic venous blood flow characterization with external cooling stimulation Infrared Physics and Technology Elsevier Science GB vol. 90 Feb. 9, 2018 Feb. 9, 2018 pp. 8-19 XP085378852.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docld/1235/file/SebastianVogtDissertation.pdf.

Thermographic venous blood flow characterization with external cooling stimulation (Year: 2018).

U.S. Appl. No. 15/650,474, filed Jul. 14, 2017 Final Office Action dated Jun. 2, 2020.

U.S. Appl. No. 15/650,474, filed Jul. 14, 2017 Non-Final Office Action dated Dec. 16, 2019.

U.S. Appl. No. 15/650,474, filed Jul. 14, 2017 Notice of Allowance dated Dec. 11, 2020.

U.S. Appl. No. 15/650,474, filed Jul. 14, 2017 Notice of Allowance dated Mar. 1, 2021.

U.S. Appl. No. 17/020,476, filed Sep. 14, 2020 Advisory Action dated Aug. 19, 2022.

U.S. Appl. No. 17/020,476, filed Sep. 14, 2020 Final Office Action dated Jan. 5, 2023.

U.S. Appl. No. 17/020,476, filed Sep. 14, 2020 Final Office Action dated Jun. 9, 2022.

U.S. Appl. No. 17/020,476, filed Sep. 14, 2020 Non-Final Office Action dated Feb. 9, 2022.

U.S. Appl. No. 17/020,476, filed Sep. 14, 2020 Non-Final Office Action dated Sep. 23, 2022.

U.S. Appl. No. 17/020,476, filed Sep. 14, 2020 Notice of Allowance dated Apr. 28, 2022.

(56) References Cited

OTHER PUBLICATIONS

U.S. Appl. No. 17/468,318, filed Sep. 7, 2021 Advisory Action dated Nov. 6, 2023.
U.S. Appl. No. 17/468,318, filed Sep. 7, 2021 Final Office Action dated Sep. 8, 2023.
U.S. Appl. No. 17/468,318, filed Sep. 7, 2021 Non-Final Office Action dated Apr. 12, 2023.
U.S. Appl. No. 17/468,318, filed Sep. 7, 2021 Notice of Allowance dated Jan. 18, 2024.
U.S. Appl. No. 17/471,015, filed Sep. 9, 2021 Advisory Action dated Feb. 2, 2024.
U.S. Appl. No. 17/471,015, filed Sep. 9, 2021 Final Office Action dated Oct. 12, 2023.
U.S. Appl. No. 17/471,015, filed Sep. 9, 2021 Non-Final Office Action dated Aug. 16, 2022.
U.S. Appl. No. 17/471,015, filed Sep. 9, 2021 Non-Final Office Action dated Mar. 28, 2024.
U.S. Appl. No. 17/471,015, filed Sep. 9, 2021 Non-Final Office Action dated Mar. 30, 2023.
U.S. Appl. No. 17/471,015, filed Sep. 9, 2021 Notice of Allowance dated Oct. 29, 2024.
U.S. Appl. No. 17/534,099, filed Nov. 23, 2021 Advisory Action dated Dec. 8, 2023.
U.S. Appl. No. 17/534,099, filed Nov. 23, 2021 Final Office Action dated Sep. 29, 2023.
U.S. Appl. No. 17/534,099, filed Nov. 23, 2021 Non-Final Office Action dated Mar. 14, 2024.
U.S. Appl. No. 17/534,099, filed Nov. 23, 2021 Non-Final Office Action dated Mar. 31, 2023.
U.S. Appl. No. 17/534,099, filed Nov. 23, 2021 Notice of Allowance dated Sep. 18, 2024.
U.S. Appl. No. 17/538,911, filed Nov. 30, 2021 Advisory Action dated Nov. 22, 2023.
U.S. Appl. No. 17/722,151, filed Apr. 15, 2022 Non-Final Office Action dated Mar. 21, 2025.
U.S. Appl. No. 17/894,460, filed Aug. 24, 2022 Advisory Action dated Mar. 13, 2025.
U.S. Appl. No. 17/973,171, filed Oct. 25, 2022 Final Office Action dated Apr. 3, 2025.
U.S. Appl. No. 17/979,601, filed Nov. 2, 2022 Notice of Allowance dated Mar. 27, 2025.
U.S. Appl. No. 17/987,698, filed Nov. 15, 2022 Advisory Action dated Feb. 21, 2025.
U.S. Appl. No. 18/113,003, filed Feb. 22, 2023 Final Office Action dated Apr. 29, 2025.
U.S. Appl. No. 18/221,318, filed Jul. 12, 2023 Restriction Requirement dated Mar. 28, 2025.
U.S. Appl. No. 18/674,601, filed May 24, 2024 Notice of Allowance dated Mar. 26, 2025.
Chen et al., 3D near infrared and ultrasound imaging of peripheral blood vessels for real-time localization and needle guidance. InMedical Image Computing and Computer-Assisted Intervention—MICCAI 2016 (pp. 388-396) (Year: 2016).
U.S. Appl. No. 17/684,180, filed Mar. 1, 2022 Final Office Action dated May 29, 2025.
U.S. Appl. No. 17/722,151, filed Apr. 15, 2022 Final Office Action dated Jul. 11, 2025.
U.S. Appl. No. 17/957,562, filed Sep. 30, 2022 Examiner's Answer dated Jun. 16, 2025.
U.S. Appl. No. 17/973,171, filed Oct. 25, 2022 Advisory Action dated Jun. 30, 2025.
U.S. Appl. No. 17/979,564, filed Nov. 2, 2022 Examiner's Answer dated May 30, 2025.
U.S. Appl. No. 17/987,698, filed Nov. 15, 2022 Non-Final Office Action dated May 23, 2025.
U.S. Appl. No. 18/113,003, filed Feb. 22, 2023 Advisory Action dated Jul. 2, 2025.
U.S. Appl. No. 18/121,802, filed Mar. 15, 2023 Notice of Allowance dated Jun. 5, 2025.
U.S. Appl. No. 18/221,318, filed Jul. 12, 2023 Non-Final Office Action dated Jun. 23, 2025.
U.S. Appl. No. 17/538,911, filed Nov. 30, 2021 Final Office Action dated Sep. 13, 2023.
U.S. Appl. No. 17/538,911, filed Nov. 30, 2021 Non-Final Office Action dated Mar. 2, 2023.
U.S. Appl. No. 17/538,911, filed Nov. 30, 2021 Notice of Allowance dated Mar. 14, 2024.
U.S. Appl. No. 17/538,943, filed Nov. 30, 2021 Non-Final Office Action dated Jan. 30, 2024.
U.S. Appl. No. 17/538,943, filed Nov. 30, 2021 Notice of Allowance dated Aug. 14, 2024.
U.S. Appl. No. 17/684,180, filed Mar. 1, 2022 Advisory Action dated Apr. 4, 2024.
U.S. Appl. No. 17/684,180, filed Mar. 1, 2022 Final Office Action dated Jan. 18, 2024.
U.S. Appl. No. 17/684,180, filed Mar. 1, 2022 Final Office Action dated Sep. 23, 2024.
U.S. Appl. No. 17/684,180, filed Mar. 1, 2022 Non-Final Office Action dated Jul. 28, 2023.
U.S. Appl. No. 17/684,180, filed Mar. 1, 2022 Non-Final Office Action dated May 8, 2024.
U.S. Appl. No. 17/684,180, filed Mar. 1, 2022 Restriction Requirement dated May 19, 2023.
U.S. Appl. No. 17/722,111, filed Apr. 15, 2022 Advisory Action dated Oct. 23, 2024.
U.S. Appl. No. 17/722,111, filed Apr. 15, 2022 Final Office Action dated Jul. 12, 2024.
U.S. Appl. No. 17/722,111, filed Apr. 15, 2022 Non-Final Office Action dated Dec. 22, 2023.
U.S. Appl. No. 17/722,151, filed Apr. 15, 2022 Advisory Action dated Jan. 2, 2024.
U.S. Appl. No. 17/722,151, filed Apr. 15, 2022 Final Office Action dated Nov. 6, 2023.
U.S. Appl. No. 17/722,151, filed Apr. 15, 2022 Final Office Action dated Sep. 20, 2024.
U.S. Appl. No. 17/722,151, filed Apr. 15, 2022 Non-Final Office Action dated Mar. 25, 2024.
U.S. Appl. No. 17/722,151, filed Apr. 15, 2022 Non-Final Office Action dated Sep. 7, 2023.
U.S. Appl. No. 17/894,460, filed Aug. 24, 2022 Advisory Action dated Apr. 4, 2024.
U.S. Appl. No. 17/894,460, filed Aug. 24, 2022 Final Office Action dated Jan. 31, 2024.
U.S. Appl. No. 17/894,460, filed Aug. 24, 2022 Non-Final Office Action dated Nov. 6, 2023.
U.S. Appl. No. 17/894,460, filed Aug. 24, 2022 Non-Final Office Action dated Sep. 25, 2024.
U.S. Appl. No. 17/957,562, filed Sep. 30, 2022 Non-Final Office Action dated Jun. 20, 2024.
U.S. Appl. No. 17/979,564, filed Nov. 2, 2022 Final Office Action dated Oct. 18, 2024.
U.S. Appl. No. 17/979,564, filed Nov. 2, 2022 Non-Final Office Action dated Jun. 5, 2024.
U.S. Appl. No. 17/979,601, filed Nov. 2, 2022 Non-Final Office Action dated Aug. 20, 2024.
U.S. Appl. No. 17/987,698, filed Nov. 15, 2022 Non-Final Office Action dated Sep. 20, 2024.
U.S. Appl. No. 18/238,281, filed Aug. 25, 2023 Non-Final Office Action dated Mar. 22, 2024.
U.S. Appl. No. 18/238,281, filed Aug. 25, 2023 Notice of Allowance dated Jul. 16, 2024.
William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.
U.S. Appl. No. 17/684,180, filed Mar. 1, 2022 Advisory Action dated Dec. 27, 2024.
U.S. Appl. No. 17/684,180, filed Mar. 1, 2022 Non-Final Office Action dated Jan. 17, 2025.
U.S. Appl. No. 17/722,111, filed Apr. 15, 2022 Notice of Allowance dated Dec. 18, 2024.

(56) References Cited

OTHER PUBLICATIONS

U.S. Appl. No. 17/722,151, filed Apr. 15, 2022 Advisory Action dated Dec. 27, 2024.
U.S. Appl. No. 17/894,460, filed Aug. 24, 2022 Final Office Action dated Dec. 31, 2024.
U.S. Appl. No. 17/957,562, filed Sep. 30, 2022 Advisory Action dated Feb. 12, 2025.
U.S. Appl. No. 17/957,562, filed Sep. 30, 2022 Final Office Action dated Nov. 27, 2024.
U.S. Appl. No. 17/973,171, filed Oct. 25, 2022 Non-Final Office Action dated Dec. 6, 2024.
U.S. Appl. No. 17/979,564, filed Nov. 2, 2022 Advisory Action dated Jan. 17, 2025.
U.S. Appl. No. 17/979,601, filed Nov. 2, 2022 Advisory Action dated Feb. 11, 2025.
U.S. Appl. No. 17/979,601, filed Nov. 2, 2022 Final Office Action dated Dec. 5, 2024.
U.S. Appl. No. 17/987,698, filed Nov. 15, 2022 Final Office Action dated Dec. 13, 2024.
U.S. Appl. No. 18/113,003, filed Feb. 22, 2023 Non-Final Office Action dated Nov. 27, 2024.
U.S. Appl. No. 18/121,802, filed Mar. 15, 2023 Non-Final Office Action dated Dec. 16, 2024.
U.S. Appl. No. 18/674,601, filed May 24, 2024 Non-Final Office Action dated Jan. 7, 2025.
Sonka, Momodou L., T. Campbell Arnold, and Ivan A. Kuznetsov. "Machine learning in point of care ultrasound." POCUS journal 7. Kidney (2022): 78. (Year: 2022).
U.S. Appl. No. 17/957,562, filed Sep. 30, 2022 Board Decision dated Apr. 22, 2026.
U.S. Appl. No. 17/957,562, filed Sep. 30, 2022 Notice of Allowance dated May 1, 2026.
U.S. Appl. No. 17/979,564, filed Nov. 2, 2022 Board Decision dated Mar. 4, 2026.
U.S. Appl. No. 17/987,698, filed Nov. 15, 2022 Non-Final Office Action dated Mar. 16, 2026.
U.S. Appl. No. 18/221,318, filed Jul. 12, 2023 Non-Final Office Action dated May 6, 2026.
U.S. Appl. No. 19/042,983, filed Jan. 31, 2025 Notice of Allowance dated Feb. 24, 2026.
U.S. Appl. No. 19/058,331, filed Feb. 20, 2025 Notice of Allowance dated Apr. 20, 2026.
Konica Minolta, "Vascular NAVI" product website. https://www.konicaminolta.com/global-en/healthcare/technology/ultrasound/vascularnavi/index.html. Last accessed Jun. 2025.
U.S. Appl. No. 17/684,180, filed Mar. 1, 2022 Advisory Action dated Aug. 25, 2025.
U.S. Appl. No. 17/684,180, filed Mar. 1, 2022 Notice of Allowance dated Sep. 30, 2025.
U.S. Appl. No. 17/722,151, filed Apr. 15, 2022 Advisory Action dated Oct. 16, 2025.
U.S. Appl. No. 17/722,151, filed Apr. 15, 2022 Non-Final Office Action dated Dec. 23, 2025.
U.S. Appl. No. 17/894,460, filed Aug. 24, 2022 Examiner's Answer dated October2, 2025.
U.S. Appl. No. 17/894,460, filed Aug. 24, 2022 Non-Final Office Action dated Jan. 14, 2026.
U.S. Appl. No. 17/973,171, filed Oct. 25, 2022 Examiner's Answer dated Jan. 28, 2026.
U.S. Appl. No. 17/987,698, filed Nov. 15, 2022 Advisory Action dated Nov. 21, 2025.
U.S. Appl. No. 17/987,698, filed Nov. 15, 2022 Final Office Action dated Sep. 12, 2025.
U.S. Appl. No. 18/113,003, filed Feb. 22, 2023 Notice of Allowance dated Aug. 15, 2025.
U.S. Appl. No. 18/221,318, filed Jul. 12, 2023 Final Office Action dated Oct. 14, 2025.
J. Nippa et al, "Pulse wave velocity in human veins", Journal of Applied Physiology, vol. 30, No. 4, pp. 558-563, Apr. 1971 (Year: 1971).
U.S. Appl. No. 17/722,151 filed Apr. 15, 2022 Notice of Allowance dated Jun. 9, 2026.
U.S. Appl. No. 17/894,460, filed Aug. 24, 2022 Final Office Action dated Jul. 21, 2026.
U.S. Appl. No. 17/979,564, filed Nov. 2, 2022 Notice of Allowance dated May 29, 2026.
U.S. Appl. No. 17/987,698, filed Nov. 15, 2022 Final Office Action dated Jun. 25, 2026.
U.S. Appl. No. 19/251,382, filed Jun. 26, 2025 Restriction Requirement dated May 18, 2026.
U.S. Appl. No. 19/290,159 filed Aug. 4, 2025 Non-Final Office Action dated Jul. 27, 2026.

* cited by examiner

AUTOMATIC VESSEL DETECTION TOOLS AND METHODS

PRIORITY

This application is a continuation of U.S. patent application Ser. No. 18/238,281, filed Aug. 25, 2023, now U.S. Pat. No. 12,138,108, which is a continuation of U.S. patent application Ser. No. 17/020,476, filed Sep. 14, 2020, now U.S. Pat. No. 11,759,166, which claims the benefit of priority to U.S. Provisional Application No. 62/903,545, filed Sep. 20, 2019, each of which is incorporated by reference in its entirety into this application.

BACKGROUND

A common challenge in administering a vascular-based therapy is finding adequate vascular access for administration of the therapy. What is needed is an ability to non-invasively identify a blood vessel suitable for administering a therapy before attempting to access the blood vessel. Satisfying such a need provides better patient outcomes by both minimizing failed attempts at vascular access and providing optimal administration of vascular-based therapies.

Disclosed herein are automatic vessel detection tools and methods that address at least the foregoing need.

SUMMARY

Briefly summarized, embodiments disclosed herein are directed to enhanced ultrasound imaging apparatus, and methods thereof, for vascular access. In particular the enhanced ultrasound image provides an automatic vessel detection system used in combination with cannula tracking.

Disclosed herein is an ultrasound system for accessing a vasculature of a patient including an ultrasound probe, a cannula, one or more processors, a display communicatively coupled to the one-or-more processors, and a non-transitory storage device communicatively coupled to the one-or-more processors. The display is for depicting an ultrasound image of a subcutaneous portion of a patient. The non-transitory storage device has stored thereon logic, that when executed by the one-or-more processors, causes performance of operations including: depicting an enhanced image of the ultrasound image, including a first icon surrounding a target vessel; receiving updated information including a dimension of the cannula; and depicting the first icon in an updated state on the enhanced image according to the updated information.

In some embodiments, the dimension of the cannula includes at least one of a longitudinal length or a diameter. The dimension of the cannula is provided by a user or derived by the ultrasound system. The first icon in the updated state includes at least one of a first color, a first pattern, a first intermittent feature, or a first alphanumerical symbol to indicate the updated state. Receiving updated information further includes measuring a diameter of the target vessel and receiving a desired range of vessel occupancy, wherein the first icon in the updated state further includes indicating a percentage vessel occupancy of the target vessel is within the desired range of vessel occupancy. Receiving updated information further includes an angle of insertion of the cannula and a desired range of vessel purchase, wherein the first icon in the updated state further includes indicating a vessel purchase length is within the desired range of vessel purchase. The angle of insertion of the cannula is predetermined. The angle of insertion of the cannula is measured by the system using at least one of a needle guide or a permanent magnet and magnetic sensor array.

In some embodiments, receiving updated information further includes measuring at least one of a Doppler information or a pulsatile information. The first icon in the updated state further includes determining a flow rate of the target vessel. The first icon in the updated state further includes determining a venous or arterial flow of the target vessel. Receiving updated information further includes measuring a change in roundness of the target vessel, wherein the first icon in the updated state further includes indicating a deviation of the roundness of the target vessel. The enhanced image of the ultrasound image further includes a guideline indicating a predicted trajectory of the cannula through the subcutaneous portion of the patient. The guideline includes at least one of a first color or a first pattern to indicate when the predicted trajectory of the cannula intersects the target vessel, as well as at least one of a second color or a second pattern to indicate when the predicted trajectory of the cannula does not intersect the target vessel.

In some embodiments, the ultrasound system further includes a second icon surrounding an obstruction disposed adjacent the trajectory of the cannula between the cannula and the target vessel. The obstruction includes at least one of a nerve bundle or an arterial vessel. The second icon includes at least one of a second color, a second pattern, a second intermittent feature, or a second alphanumerical symbol. The enhanced image of the ultrasound image further includes an alert indicating a tip of the cannula is proximate a back wall of the target vessel.

Also disclosed herein is a method of accessing a vessel using ultrasonic imaging including providing an ultrasound system; depicting an enhanced image of an ultrasound image including a first icon surrounding a target vessel; receiving updated information including a dimension of the cannula; and depicting the first icon in an updated state on the enhanced image according to the updated information. The ultrasound system includes an ultrasound probe, a cannula, one or more processors, a display communicatively coupled to the one-or-more processors, and a non-transitory storage device communicatively coupled to the one-or-more processors. The display is configured for depicting the ultrasound image or the enhanced ultrasound image of a subcutaneous portion of a patient.

In some embodiments, the dimension of the cannula includes at least one of a longitudinal length or a diameter. The first icon in the updated state includes at least one of a first color, a first pattern, a first intermittent feature, or a first alphanumerical symbol to indicate the updated state. Receiving updated information further includes measuring a diameter of the target vessel and receiving a desired range of vessel occupancy, wherein the first icon in the updated state further includes indicating a percentage vessel occupancy of the target vessel is within the desired range of vessel occupancy. Receiving updated information further includes an angle of insertion of the cannula and a desired range of vessel purchase, wherein the first icon in the updated state further includes indicating a vessel purchase length is within the desired range of vessel purchase. The angle of insertion of the cannula is measured by the system using at least one of a needle guide or a permanent magnet and magnetic sensor array.

In some embodiments, receiving updated information further includes measuring a change in roundness of the target vessel, wherein the first icon in the updated state further includes indicating a deviation of the roundness of the target vessel. The enhanced image of the ultrasound image further includes a guideline indicating a predicted trajectory of the cannula through the subcutaneous portion of the patient. The guideline includes at least one of a first color or a first pattern to indicate when the predicted trajectory of the cannula intersects the target vessel, as well as at least one of a second color or a second pattern to indicate when the predicted trajectory of the cannula does not intersect the target vessel.

In some embodiments, the method of accessing a vessel using ultrasonic imaging further includes a second icon surrounding an obstruction disposed adjacent the trajectory of the cannula between the cannula and the target vessel. The obstruction includes at least one of a nerve bundle or an arterial vessel. The second icon includes at least one of a second color, a second pattern, a second intermittent feature, or a second alphanumerical symbol. The enhanced image of the ultrasound image further includes an alert indicating a tip of the cannula is proximate a back wall of the target vessel.

These and other features of the concepts provided herein will become more apparent to those of skill in the art in view of the accompanying drawings and following description, which disclose particular embodiments of such concepts in greater detail.

DESCRIPTION

Figure 1A:
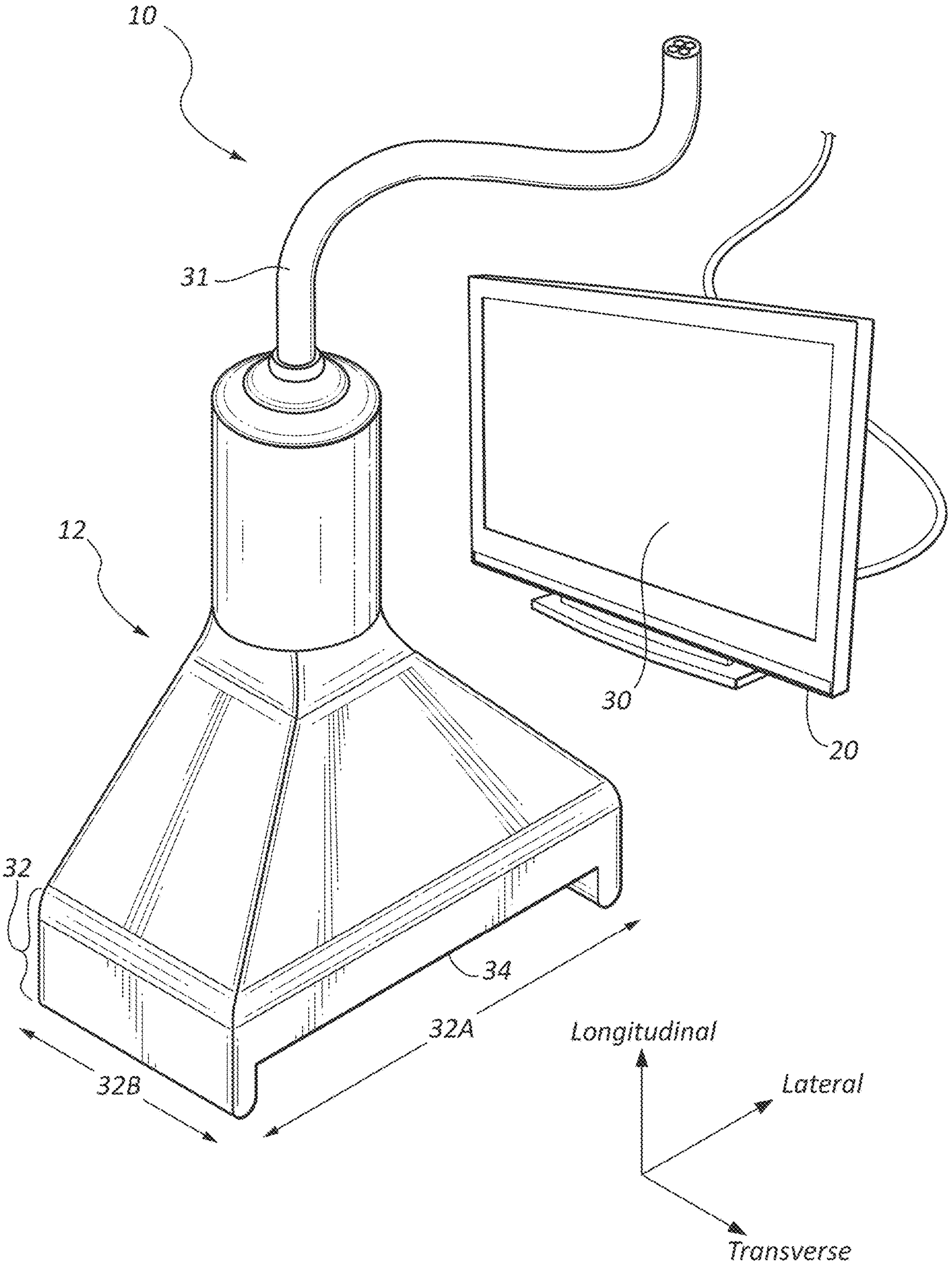
FIG. 1A illustrates an example ultrasound system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, “first,” “second,” and “third” features or steps need not necessarily appear in that order, and the particular embodiments including such features or steps need not necessarily be limited to the three features or steps. Labels such as “left,” “right,” “top,” “bottom,” “front,” “back,” and the like are used for convenience and are not intended to imply, for example, any particular fixed location, orientation, or direction. Instead, such labels are used to reflect, for example, relative location, orientation, or directions. Singular forms of “a,” “an,” and “the” include plural references unless the context clearly dictates otherwise.

With respect to “proximal,” a “proximal portion” or a “proximal end portion” of, for example, a catheter disclosed herein includes a portion of the catheter intended to be near a clinician, or user, when the catheter is used on a patient. Likewise, a “proximal length” of, for example, the catheter includes a length of the catheter intended to be near the clinician when the catheter is used on the patient. A “proximal end” of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to “distal,” a “distal portion” or a “distal end portion” of, for example, a catheter disclosed herein includes a portion of the catheter intended to be near or in a patient when the catheter is used on the patient. Likewise, a “distal length” of, for example, the catheter includes a length of the catheter intended to be near or in the patient when the catheter is used on the patient. A “distal end” of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

As shown in FIG. 1A, and to assist in the description of the components of embodiments described herein, the ultrasound probe is described in terms of being held vertically with an acoustic surface being held against a horizontal surface, for example, a skin surface of a patient. The longitudinal axis extends perpendicular to the acoustic surface. The acoustic surface is defined by the lateral and transverse axes, with the lateral axis extending normal to the longitudinal axis, and the transverse axis extending normal to both the lateral and longitudinal axis. As used herein, the term "cannula" refers to an elongate medical device, or medical device assembly, that can be inserted subcutaneously to access a vasculature of the patient. Example cannulae can include, but not limited to needles, catheters, stylets, guidewires, trocars, combinations thereof, and the like. As used herein in a "vessel" refers to a given portion of a vascular system for a patient. While embodiments are described herein in reference to a blood vessel, it will be appreciated that aspects of the invention can be applied to various other vasculature systems, body cavities, and the like.

As used herein, the terms "logic" and "component" are representative of hardware, firmware and/or software that is configured to perform one or more functions. As hardware, logic (or a component) may include circuitry having data processing or storage functionality. Examples of such processing or storage circuitry may include, but is not limited or restricted to the following: a processor; one or more processor cores; a programmable gate array; an I/O controller (e.g., network interface controller, disk controller, memory controller, etc.); an application specific integrated circuit; receiver, transmitter and/or transceiver circuitry; semiconductor memory; combinatorial logic, or combinations of one or more of the above components.

Logic (or a component) may be in the form of one or more software modules, such as executable code in the form of an operating system component, an executable application, firmware, an application programming interface (API), one or more subroutines, a function, a procedure, an applet, a plug-in, a servlet, a Component Object Model (COM) object, a routine, source code, object code, a shared library/dynamic linked library, a script, or one or more instructions. These software modules may be stored in any type of a suitable non-transitory storage medium, or transitory storage medium (e.g., electrical, optical, acoustical, or other form of propagated signals such as carrier waves, infrared signals, or digital signals). Examples of a "non-transitory storage medium" may include, but are not limited or restricted to a programmable circuit; non-persistent storage such as volatile memory (e.g., any type of random access memory "RAM"); persistent storage such as non-volatile memory (e.g., read-only memory "ROM", power-backed RAM, flash memory, phase-change memory, etc.), a solid-state drive, hard disk drive, an optical disc drive, or portable memory device; and/or a semiconductor memory. As firmware, the executable code is stored in persistent storage.

A "computing system" generally refers to either a physical electronic device featuring data processing and/or network connection functionality or a virtual electronic device being software that virtualizes at least a portion of the functionality of the physical electronic device. Examples of a computing system may include, but are not limited or restricted to any physical or virtual resource operating as a server, a network device (e.g., a mobile phone, a desktop or laptop computer, a wearable, a set-top box, a tablet, a netbook, a server, a device-installed mobile software, management console, etc.), a network adapter, or an intermediary communication device (e.g., router, firewall, etc.), a cloud service, or the like. Additional examples of a network device may include, but are not limited or restricted to the following: a server; a router or other signal propagation networking equipment (e.g., a wireless or wired access point); a set-top box; a video-game console; or an endpoint (e.g., a stationary or portable computer including a desktop computer, laptop, electronic reader, netbook or tablet; a smart phone; or wearable technology such as an Apple Watch®, Fitbit® fitness wristband, or other sensor-based component, including any sensors configured for participation within an internet-of-things (IoT) environment).

Unless defined otherwise, all technical and scientific terms used herein have the same meaning as commonly understood by those of ordinary skill in the art.

As set forth above, an ability to non-invasively identify a blood vessel suitable for administering a therapy is needed. Satisfying such a need provides better patient outcomes by both minimizing failed attempts at vascular access and providing optimal administration of vascular-based therapies.

Disclosed herein are automatic vessel detection tools and methods that address at least the foregoing need. Indeed, as set forth below, ultrasound imaging combined with image processing provide valuable information to clinicians for providing administration of vascular-based therapies.

Figure 1B:
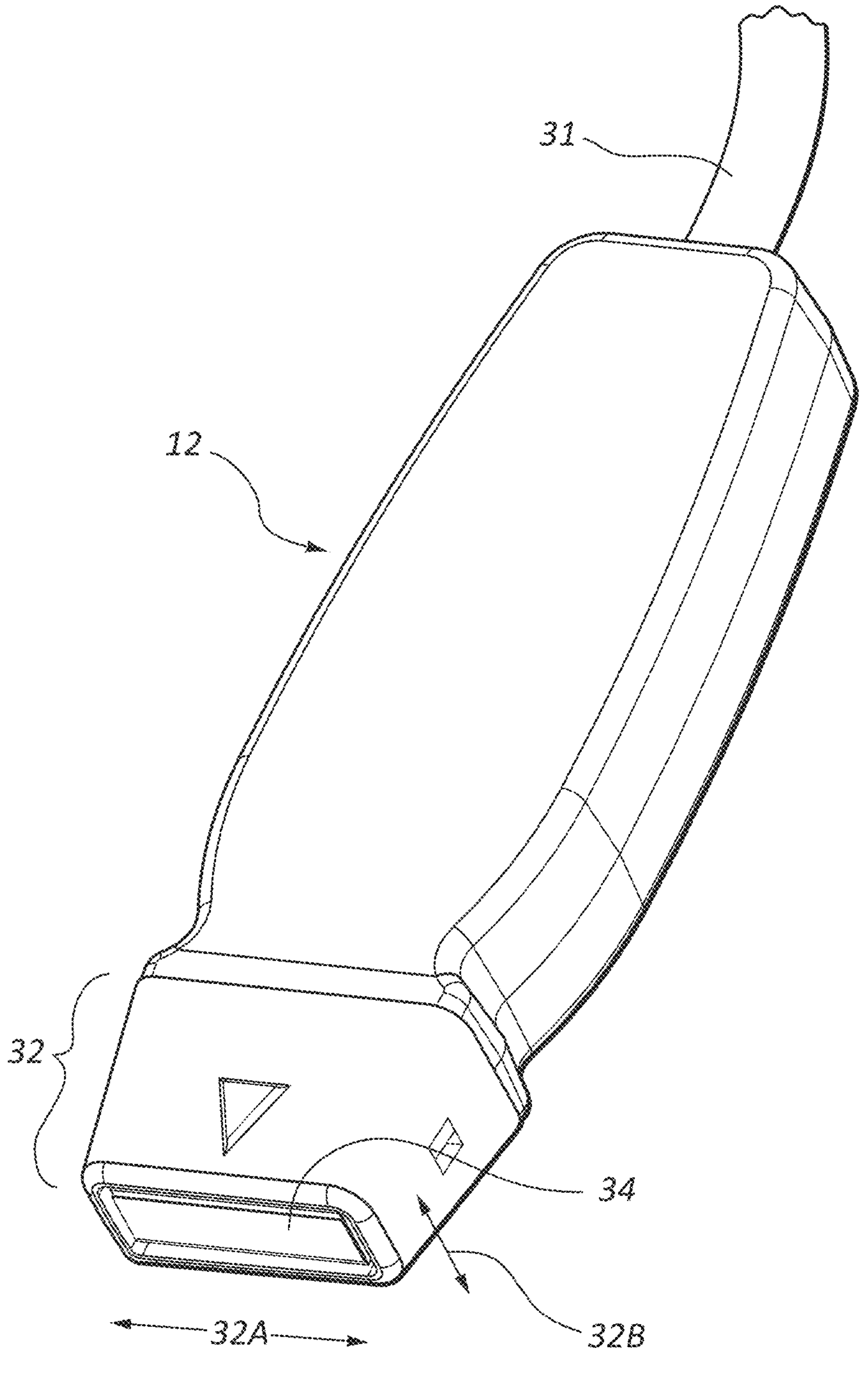
FIG. 1B illustrates an example ultrasound probe, in accordance with embodiments disclosed herein.
Figure 1C:
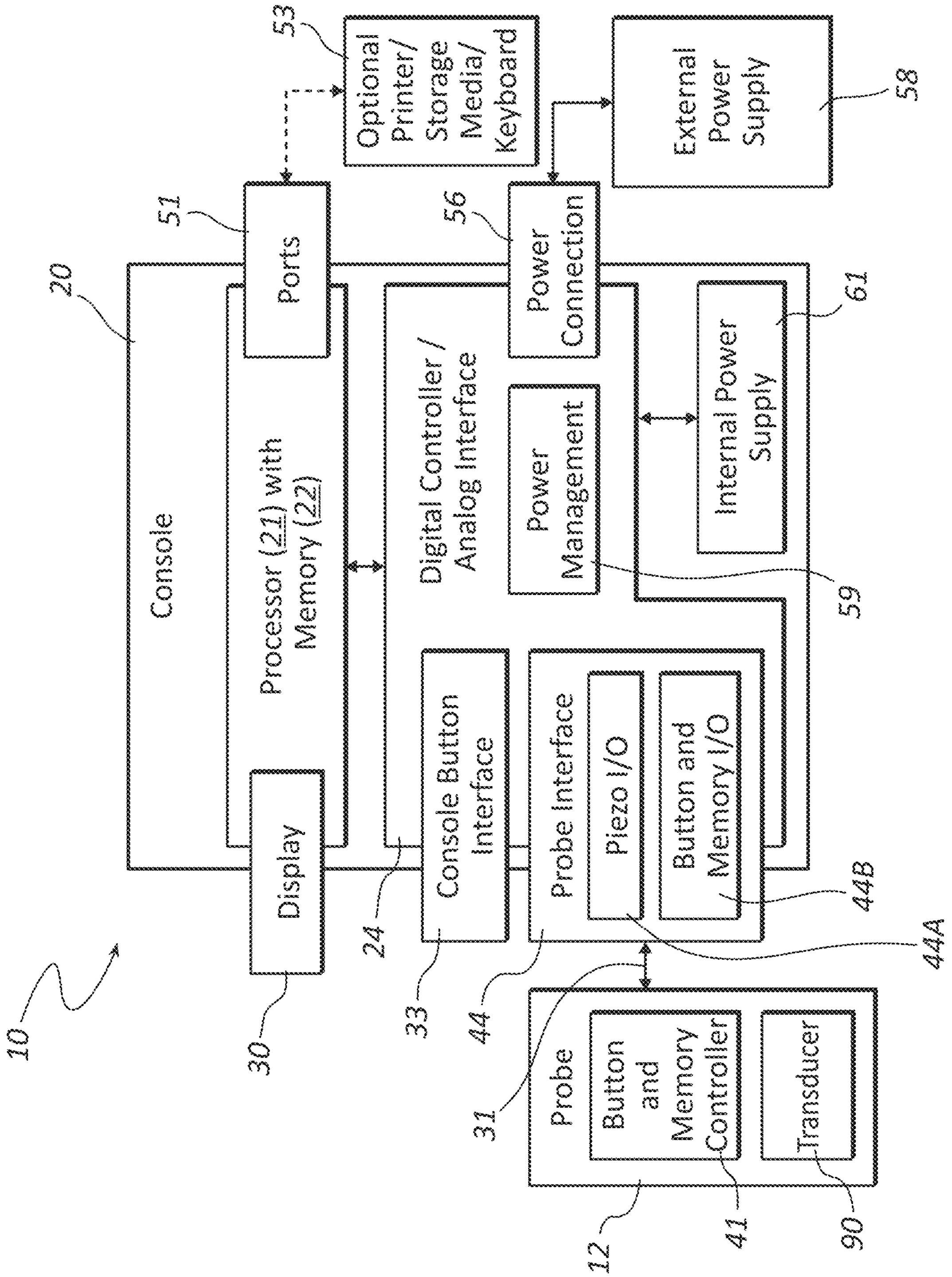
FIG. 1C illustrates a block diagram of the ultrasound probe coupled to the ultrasound system, in accordance with embodiments disclosed herein.

FIGS. 1A-1C show example embodiments of an ultrasound imaging system 10 that generally includes an ultrasound probe 12 and a console 20 including a display 30 for depicting an image produced by the ultrasound probe 12. It will be appreciated that the console 20 can take one of a variety of forms. A processor 21 together with non-volatile memory 22 (e.g., EEPROM) is included in the console 20 for controlling system function during operation of the system 10, thus acting as a control processor. A digital controller/analog interface 24 is also included with the console 20 and is in communication with both the processor 21 and other system components to govern interfacing between the ultrasound probe 12, transducer 90, optional magnetic sensors, and other system components.

The system 10 can further include a plurality of ports 51 for connection with optional components 53 including a printer, storage media, keyboard, etc. The ports in one embodiment are USB ports, though other port types or a combination of port types can be used for this and the other interfaces connections. In certain embodiments, the ports 51 may be implemented via a wireless connection over a network. A power connection 56 is included with the console 20 to enable operable connection to an external power supply 58. An internal power supply 61 (e.g., a battery) can also be employed, either with or exclusive of an external power supply. Power management circuitry 59 is included with the digital controller/analog interface 24 of the console to regulate power use and distribution.

The display 30 can be a single stand-alone display or an integrated display integrated into the console 20 for displaying information to a clinician. (See FIGS. 2A, 2B, 3A, etc.) As set forth below, the content depicted by the display 30 can change in accordance with different ultrasound image enhancements. In certain embodiments, a console button interface 33 and buttons included on the ultrasound probe 12 can be used to immediately call up a desired mode to the display 30 with ultrasound image enhancements for the clinician to assist in the procedure.

Those skilled in the art will appreciate that the embodiments of the present invention may be practiced in computing environments with one or more types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, and the like. Embodiments may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

In an embodiment, the ultrasound probe 12 is operably connected to the console 20 via a cable 31, though in an embodiment the ultrasound probe 12 can be wirelessly connected thereto. The ultrasound probe 12 includes a head portion ("probe head," or "head") 32 defined by a lateral length 32A and a transverse width 32B. The probe head 32 includes an acoustic surface 34 extending along at least a portion of the lateral length 32A of the probe head from which ultrasonic impulses are emitted by the transducer 90, disposed within the probe head 32, in order to penetrate and image subcutaneous portions of the patient. Note that the size, shape, and configuration of both the ultrasound probe 12, probe head 32, transducer 90, and acoustic surface 34 can vary from what is described herein while still residing within the principles of the present disclosure. Note also that FIGS. 1A-1C show example ultrasound imaging systems; other systems including other components can also benefit from the principles described herein.

FIG. 1C further shows that the ultrasound probe 12 can further include a button and memory controller 41 for governing button and probe operation. The button and memory controller 41 can include non-volatile memory, such as EEPROM, in certain embodiments. The button and memory controller 41 is in operable communication with a probe interface 44 of the console 20, which often includes a piezo input/output component 44A for interfacing with the probe piezoelectric array and a button and memory input/output component 44B for interfacing with the button and memory controller 41.

Figure 2A:
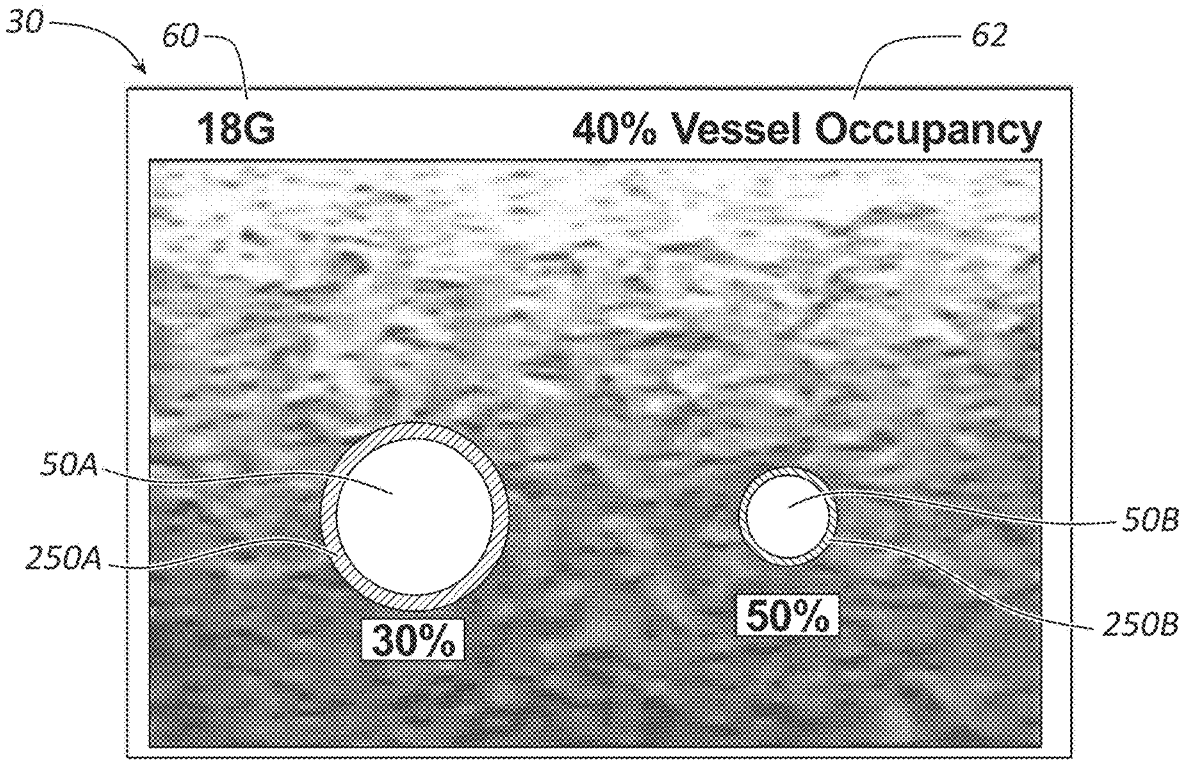
FIG. 2A illustrates an enhanced ultrasound image including blood vessel iconography for medical device occupancy, in accordance with embodiments disclosed herein.
Figure 2B:
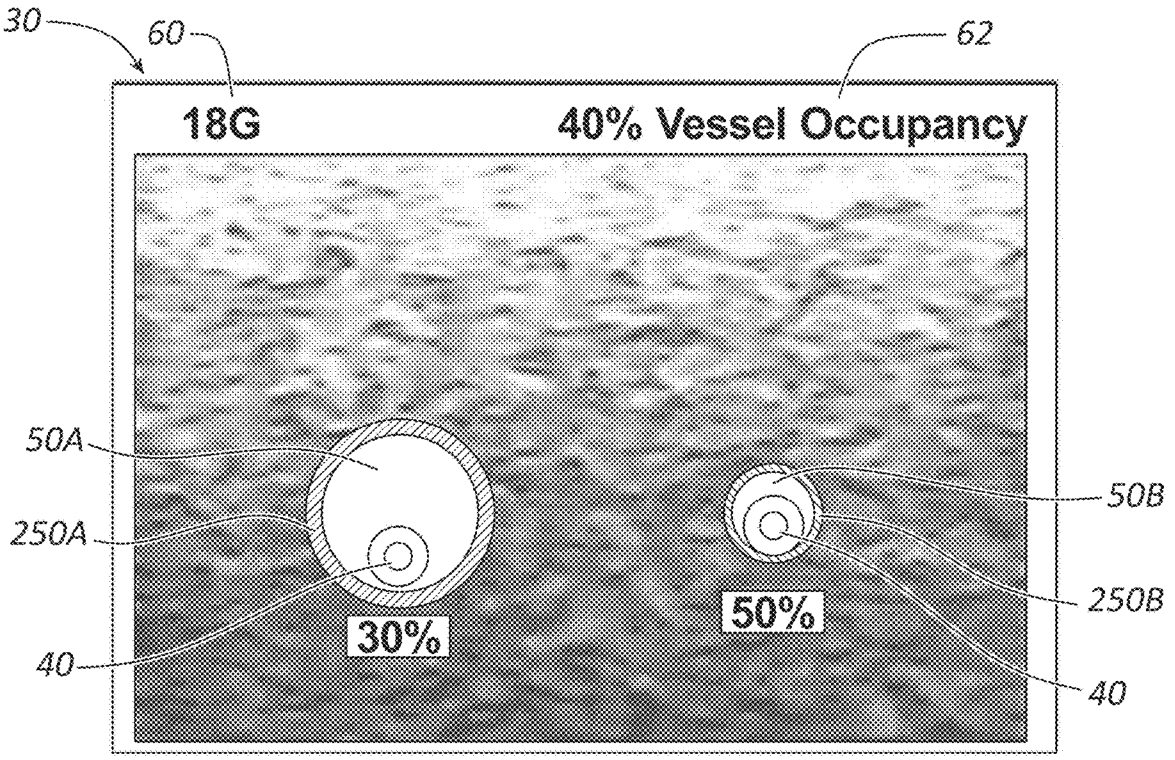
FIG. 2B illustrates the enhanced ultrasound image of FIG. 2A further including medical device iconography, in accordance with embodiments disclosed herein.

In an embodiment, as shown in FIGS. 2A-2B, the display 30 depicts an enhanced ultrasound image including an imaged subcutaneous portion of a patient, and one or more icons each surrounding a target area, for example a target vessel 50. The system 10 autonomously determines target structures within the image and positions the icon accordingly. The icon can identify potential target vessels within the image and clearly distinguish these vessels from surrounding structures to make them easily and quickly identifiable. The icon includes one or more colors, patterns, intermittent ("flashing" or "blinking") features, alphanumeric symbols, combinations thereof, or the like, to further distinguish the target vessel 50 from surrounding imaged structures. The icon further includes an updated state which includes a change in the one-or-more colors, patterns, intermittent features, alphanumeric symbols, combinations thereof, or the like that indicates to a clinician information regarding the target vessel the icon is associated with. The enhanced image can also display additional icons representing, for example, a cannula 40, or tip thereof 42, guidelines, trajectory ranges of the cannula, and potential obstructions.

In an embodiment, the enhanced image can further display additional information, for example, cannula size 60, angle of insertion 64 of the cannula relative to the ultrasound probe 12, and the like. In an embodiment, the cannula size is entered to the system 10 by the clinician. In an embodiment, the system 10 receives or derives the cannula size from RFID chips, magnetic sensor arrays, and the like. For example, the cannula can include identification markers, RFID chips, barcodes, QR codes, combinations thereof, or the like, that include information about the size, diameter, length, etc. of the cannula being used. The system 10 interprets the size of cannula being used by way of these identification markers and the like, independent of any input from the clinician.

In an embodiment, the angle of insertion of the cannula is entered to the system 10 by the clinician. In an embodiment, the system 10 is able to determine the angle of insertion by detecting the presence of the cannula within an angled needle guide, coupled to the ultrasound probe 12. In an embodiment, the cannula includes at least one of a permanent magnet, an electromagnet, an optical marker, or acoustic marker, or the like, which is detected by a magnetic sensor array and can determined the location and orientation of the cannula in three-dimensional space. Further details of enhanced ultrasound imaging, and associated features, can be found, for example, in U.S. 2018/0015256, filed Jul. 14, 2017 and U.S. Pat. No. 9,949,720, filed Oct. 19, 2012, each of which are incorporated by reference in its entirety into this application.

In an embodiment, as shown in FIGS. 2A-2B, the enhanced image depicted on the display 30 indicates a first icon 250A highlighting the target vessel 50. To note, the system 10 autonomously identifies one or more target vessels within the image and positions one or more icons surrounding the one-or-more target vessels. The system 10 can measure the diameter of the target vessel and, together with information on the cannula size 60 of the cannula being used, determine a percentage vessel occupancy for the target vessel. For example, as shown, the first icon 250A highlights a first target vessel 50A, and determines a vessel occupancy of 30% with an 18-gauge cannula. A second icon 250B highlights a second target vessel 50B, and determines a 50% vessel occupancy with an 18-gauge cannula.

In an embodiment, the system 10 can receive further information about a desired vessel occupancy range 62, for example, 40%. In an embodiment, the desired vessel occupancy range is entered by the clinician. In an embodiment, the desired vessel occupancy range derived from patient specific data. For example, based on the procedure being performed, age, weight, gender of the patient, combinations thereof, or the like. The system 10, then provides the icons 250A and 250B in an updated state to indicate if the target vessel is within the desired range. For example, the first icon 250A provides a first color, pattern, and label, while the second icon 250B which is outside of the desired range provides a second color, pattern, and label. FIG. 2B shows the target vessels with the cannula 40 disposed in each to illustrate the percentage vessel occupancy.

Figure 3A:
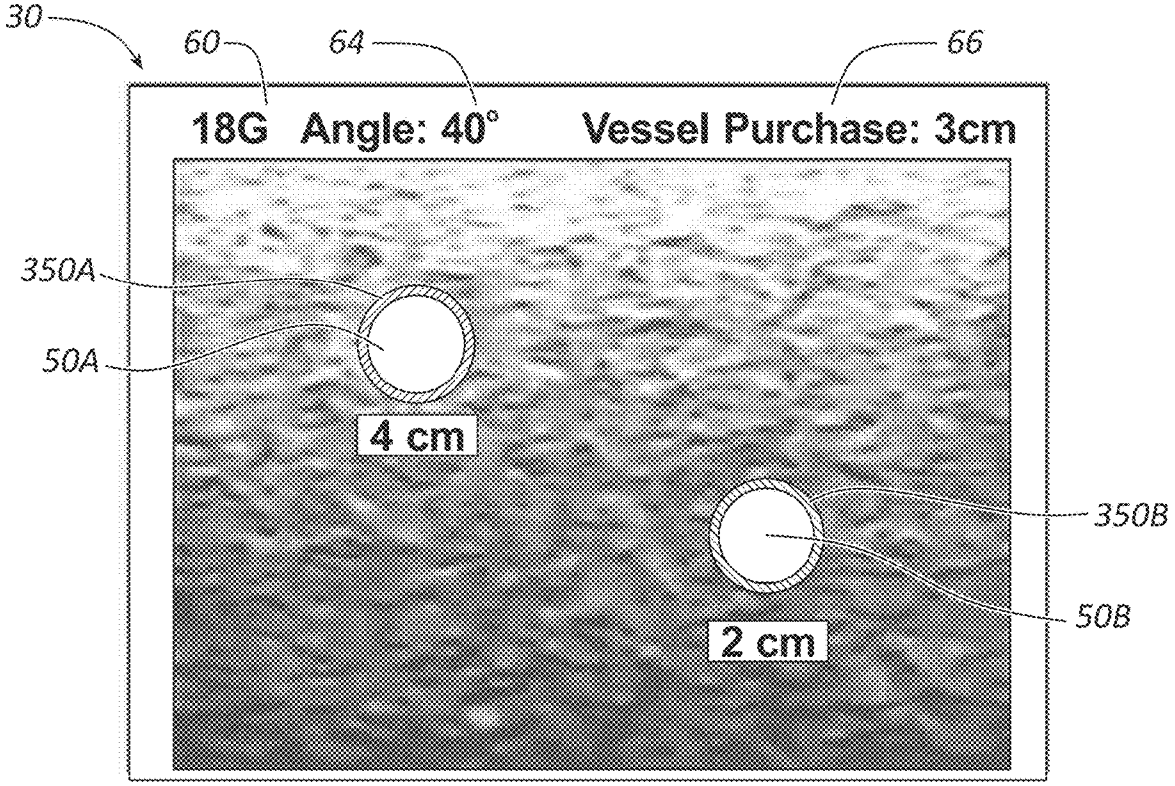
FIG. 3A illustrates an enhanced ultrasound image including blood vessel iconography for purchase length, in accordance with embodiments disclosed herein.

In an embodiment, as shown in FIG. 3A, the enhanced image depicted on the display 30 indicates a first icon 350A highlighting the first target vessel 50A. The system 10 can measure the depth of the target vessel relative to the skin surface and, together with information on the cannula size 60 of the cannula being used and the angle of insertion 64, determine a vessel purchase length for the target vessel. For example, as shown, the first icon 350A highlights the first target vessel 50A, and determines a vessel purchase length of 4 cm. A second icon 350B highlights a second target vessel 50B, and determines a 2 cm vessel purchase length.

Figure 3B:
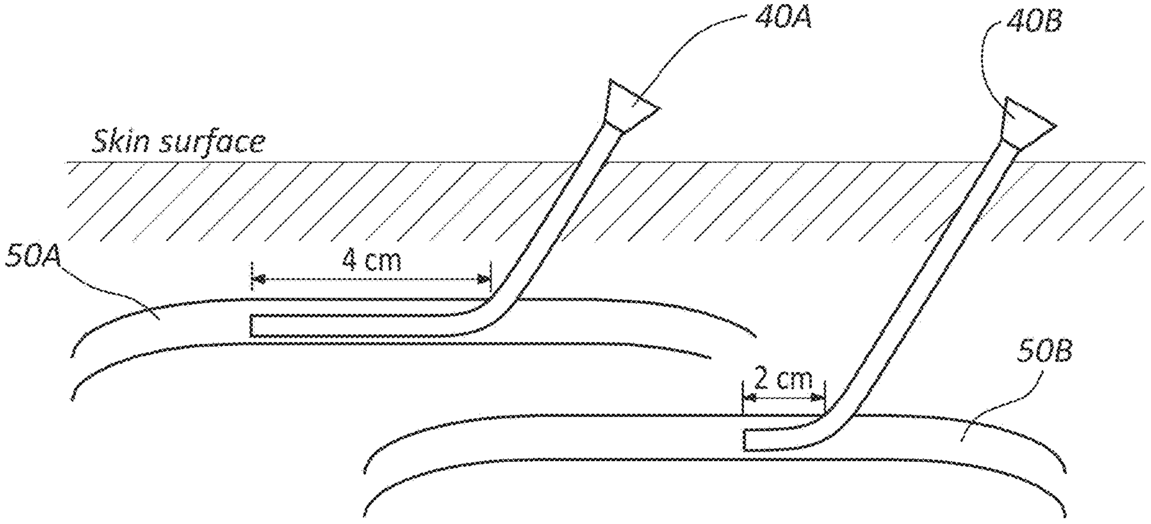
FIG. 3B illustrates a cross sectional view of cannulae disposed within the vessels referenced in FIG. 3A, in accordance with embodiments disclosed herein.

In an embodiment, the system 10 receives further information about a desired vessel purchase length 66, for example, 3 cm. In an embodiment, the desired vessel purchase length is entered by the clinician. In an embodiment, the desired vessel purchase length is derived from patient specific data. For example, based on the procedure being performed, age, weight, gender of the patient, combinations thereof, or the like. The system 10, then provides the icons 350A and 350B in an updated state to indicate if the target vessel is within the desired range, as described herein. FIG. 3B illustrates the target vessels 50A and 50B respectively with a cannula 40A and 40B disposed therein to illustrate how the vessel purchase length varies with depth of the target vessel. To note, embodiments described herein can be combined such that a user can enter both a desired vessel occupancy range and a desired vessel purchase range and icons can be provided in an updated state to indicate the one or both of these requirements are met. Further, it will be appreciated, that additional embodiments described herein can also be combined in a similar manner without departing from the spirit of the invention.

Figure 4A:
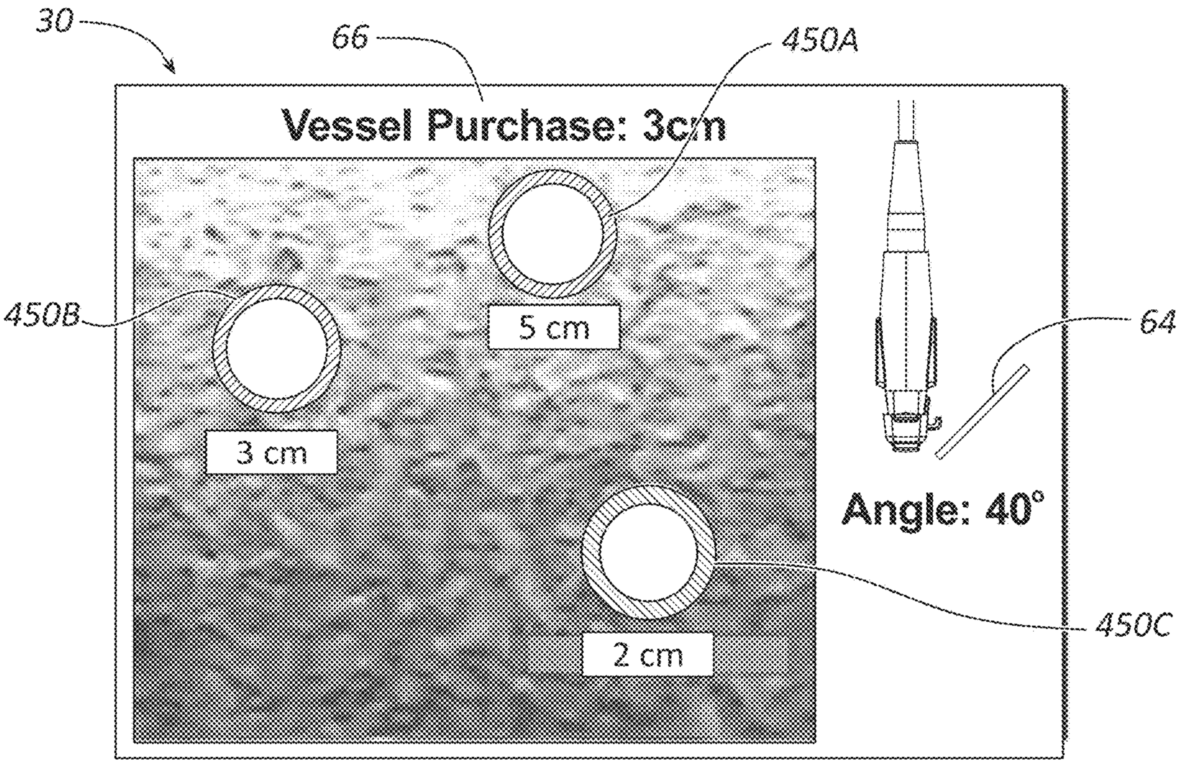
FIG. 4A illustrates an enhanced ultrasound image including blood vessel iconography for a first insertion angle, in accordance with embodiments disclosed herein.

In an embodiment, a variation in insertion angle can further affect which vessels are within range. As shown in FIG. 4A, the needle is provided at a 40° angle. The system 10 can determine this angle by way of a needle guide, permanent magnet and magnetic sensor array, markers, or the like, as disclosed herein. The console then provides an enhanced image to indicate which of the vessels imaged are within the desired vessel purchase range. As shown, a first icon 450A and a second icon 450B highlight vessels and indicates they are within a desired vessel purchase range, as described herein. A third icon 450C highlights a third vessel and indicates that while it is possible to be accessed, it would only allow a 2 cm vessel purchase length which is outside of the desired range, and is therefore indicated as such.

Figure 4B:
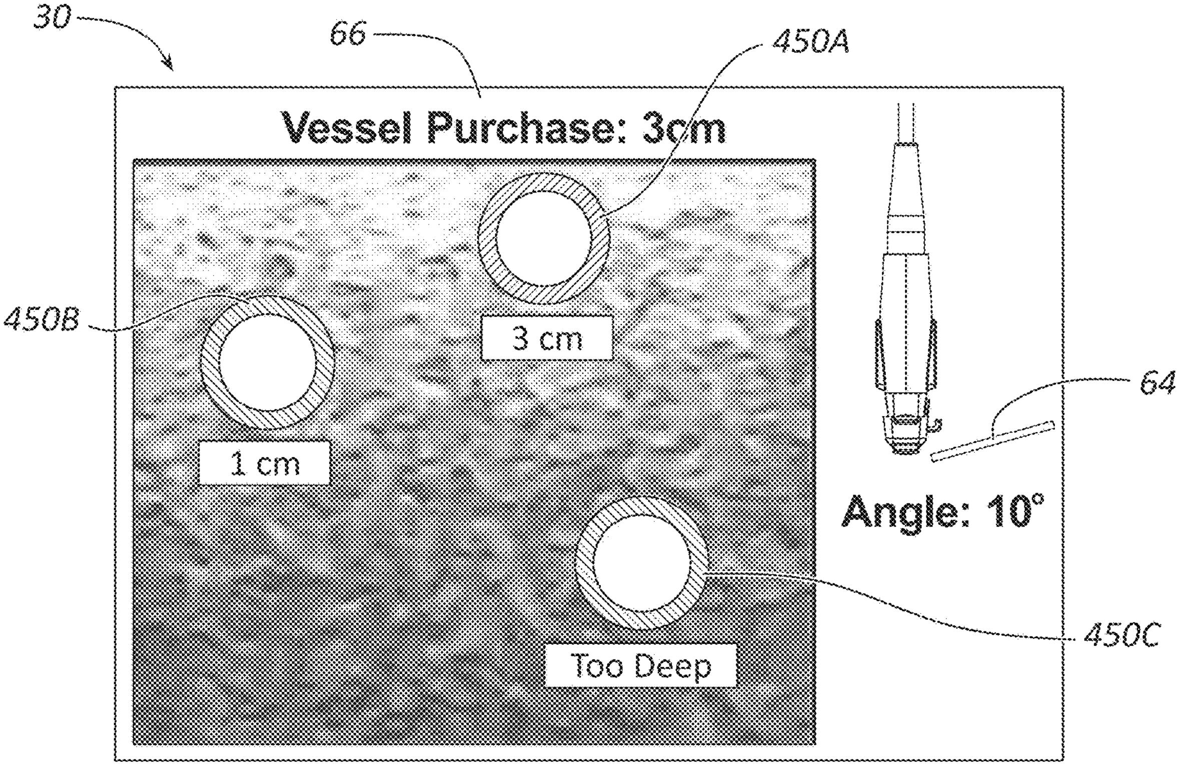
FIG. 4B illustrates enhanced ultrasound image including blood vessel iconography for a second insertion angle, in accordance with embodiments disclosed herein.

FIG. 4B shows the cannula being inserted at a shallower angle, for example, 10°, than that shown in FIG. 4A, which limits the depth accessible by the cannula. Accordingly, the first vessel highlighted by the first icon 450A is still accessible and still within the desired vessel purchase range, albeit with less absolute vessel purchase length. The second vessel, highlighted by the second icon 450B, is now outside of the desired vessel purchase range and is indicated as such. The third vessel, highlighted by icon 450C is now too deep to access at all, and is also indicated as such on the screen.

Figure 5A:
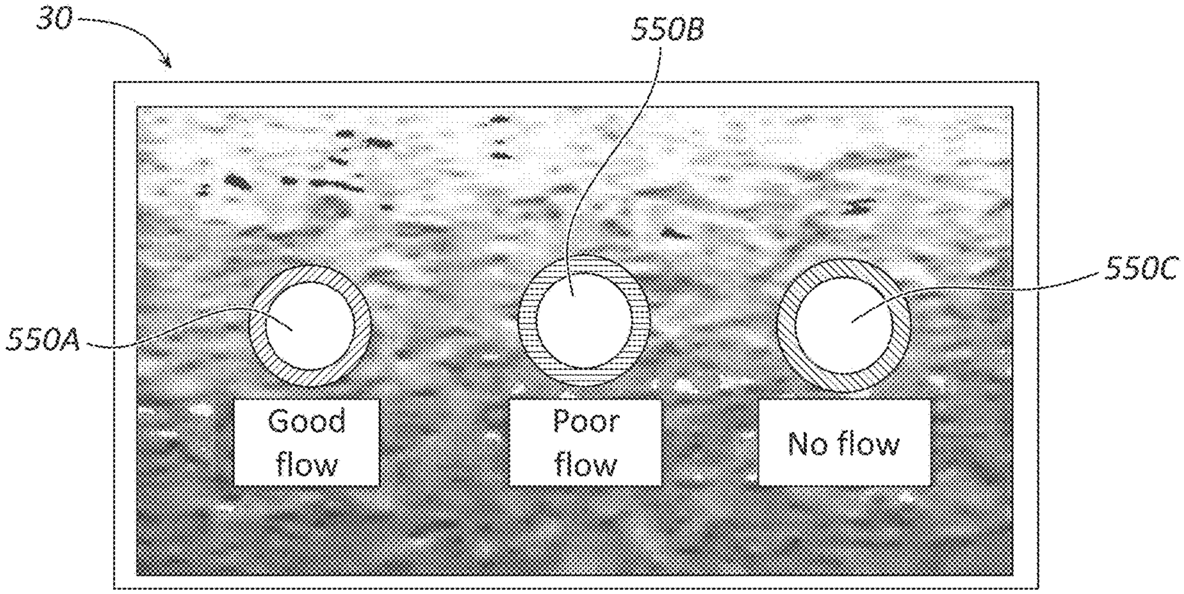
FIG. 5A illustrates an enhanced ultrasound image including blood vessel iconography for a vessel-flow characteristics, in accordance with embodiments disclosed herein.
Figure 5B:
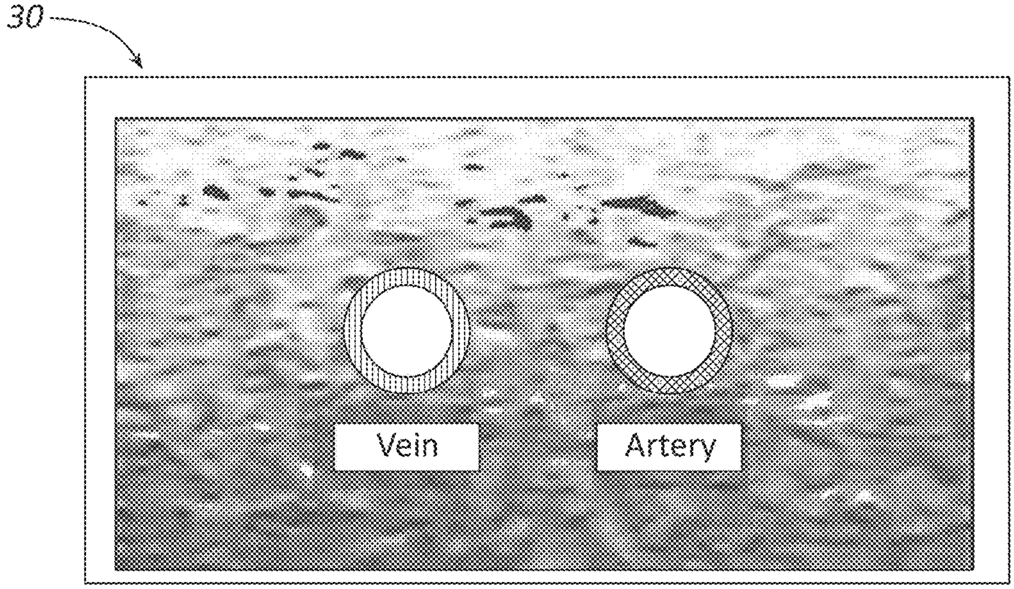
FIG. 5B illustrates an enhanced ultrasound image including blood vessel iconography for a venous-arterial differentiation, in accordance with embodiments disclosed herein.

In an embodiment, as shown in FIGS. 5A-5B the system 10 determines flow characteristics of the target vessels being imaged and provides icons in an updated state to indicate these features to the clinician. For example, the system 10 includes Doppler measurements, pulsatile measurements, combinations thereof, or the like to determine if the vessel has sufficient flow for a procedure. As shown in FIG. 5A, a first icon 550A indicates a first target vessel has sufficient flow ("good flow") using a first color, pattern, label, or combinations thereof. A second icon 550B indicates a second vessel has "poor flow" using a second color, pattern, label, or combinations thereof. Similarly, a third icon 550C indicates a third vessel as having "no flow" using a third color, pattern, label, or combinations thereof. Further, as shown in FIG. 5B, the system 10 can determine if the target vessel is either venous or arterial, through Doppler measurements of a fluid flow through the vessel, the presence or absence of pulsatile movements of the vessel, or combinations thereof. Accordingly, the icons can include colors, patterns, labels, or combinations thereof, to indicate as such.

In an embodiment, the system 10 provides feedback to the clinician directed to the positioning of the probe. For example, the system 10 identifies the location of a target vessel, depicted on the display 30, and determines if the target vessel is "moving." If so, this would indicate that the ultrasound probe 12 is not being held steady enough. Such movement can be outside of tolerance levels that equate to normal bodily movements from the patient, such as breathing or pulsatile movements from the vessel, or the like. Accordingly, visual, audible, or tactile alerts can be provided to the clinician advising to "adjust position of the probe," "hold the probe steady", or the like. It will be appreciated that visual alerts can include messages, notices, icons, alphanumeric symbols, colors, or the like, depicted on the display 30. Further, visual alerts can include LED lights, indicators, or the like, operably connected with the system 10 that visually alert the clinician. Audible alerts can include sounds, instructions, alarms, or the like. Tactile alerts can include vibrations transmitted through portions of the system 10 being held by the clinician.

Figure 6:
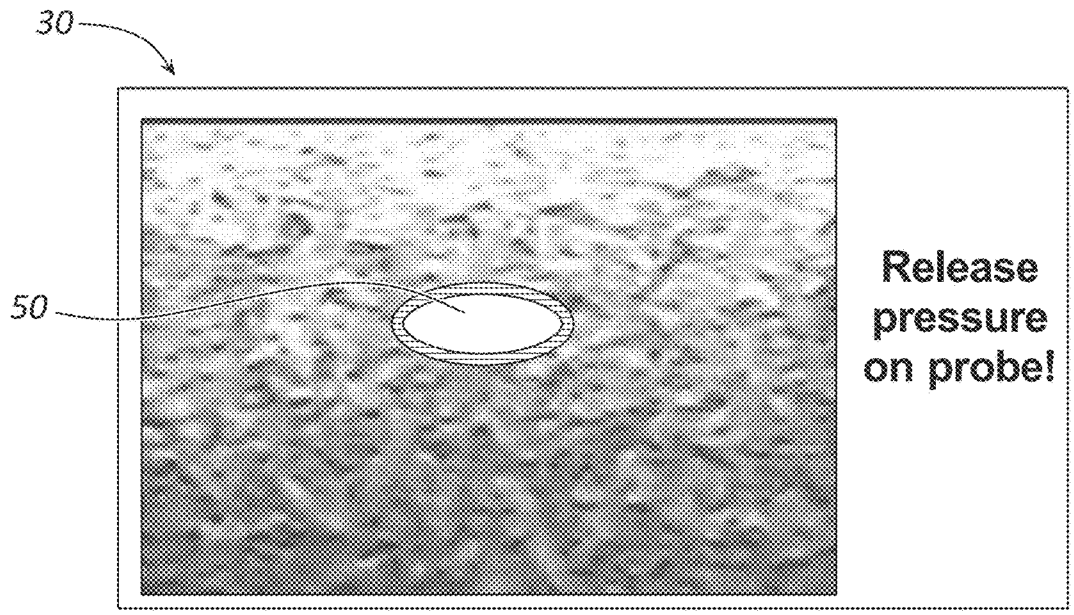
FIG. 6 illustrates an enhanced ultrasound image including blood vessel iconography for roundness of a blood vessel, in accordance with embodiments disclosed herein.

In an embodiment, as shown in FIG. 6, the system 10 can measure the roundness of a target vessel, or changes thereof, to determine if the pressure of the ultrasound probe 12 against the skin surface is affecting the patency of the target vessel 50. If the roundness of the vessel 50 deviates from acceptable tolerance levels, the system can provide visual, audible, or tactile alerts, as described herein, to "release pressure on probe" or the like.

Figure 7:
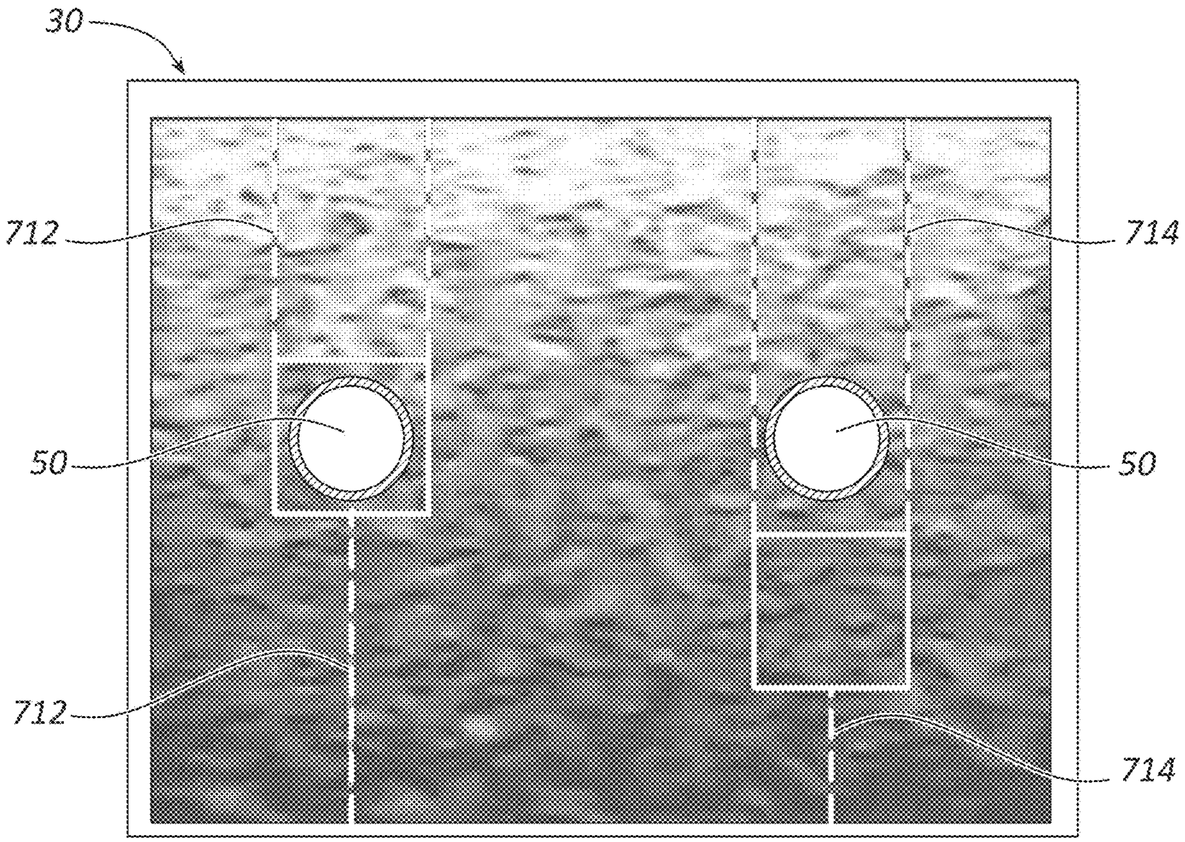
FIG. 7 illustrates an enhanced ultrasound image including guidelines for predicted trajectories to target blood vessels, in accordance with embodiments disclosed herein.

In an embodiment, as shown in FIG. 7, the system 10 provides guidelines, for example, guidelines 712 and 714, superimposed on the ultrasound image to indicate a predicted trajectory of the cannula 40, relative to the target vessel 50. As discussed herein, the system 10 can determine the position and orientation of the cannula 40 relative to the ultrasound probe 12, for example using needle guides or magnetic sensor arrays. Accordingly, the system 10 can display a predicted trajectory of the cannula by the guideline 712, or range of trajectory, relative to the target vessel 50, and indicate with colors, patterns, or instructions displayed proximate thereto if the cannula is on course to access the target vessel. Where the cannula is not on course to access the vessel, the guideline 714 can indicate as such through different colors, patterns, or instructions displayed proximate thereto.

Figure 8:
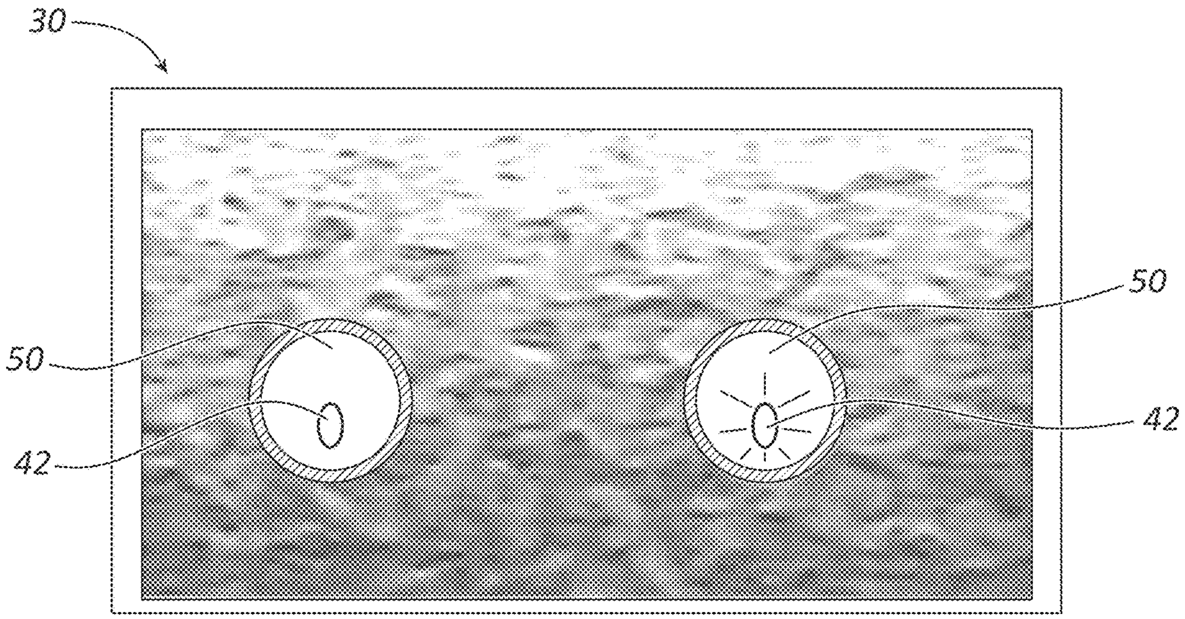
FIG. 8 illustrates an enhanced ultrasound image including blood vessel and medical device iconography upon access to the blood vessel, in accordance with embodiments disclosed herein.
Figure 9:
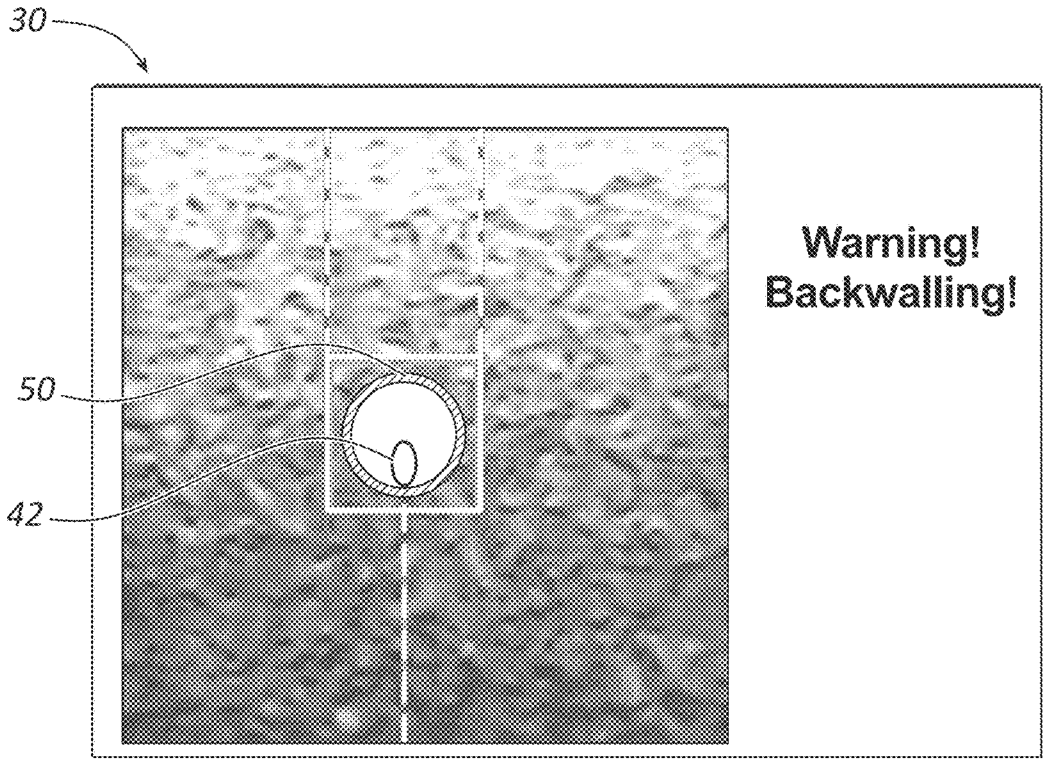
FIG. 9 illustrates an enhanced ultrasound image including blood vessel and medical device iconography for predicted procedural errors such as backwalling, in accordance with embodiments disclosed herein.

In an embodiment, as shown in FIGS. 8-9, the system 10 can determine the location of the cannula tip 42 of the cannula 40 in three-dimensional space, as discussed herein. As shown in FIG. 8, the cannula tip 42 can include additional color, patterns, highlights, and the like to indicate to the clinician a successful accessing of the vessel. In an embodiment, as shown in FIG. 9, the system can determine if the cannula tip 42 is proximate to a lower wall of the target vessel 50. As such, the system 10 can provide visual, audible, or tactile alerts, as described herein, to indicate the cannula can potentially be inserted through a far wall of the vessel, termed "backwalling." The cannula tip 42 can be represented as an image, symbol, icon, or the like, and can be depicted with a distinct color, pattern, highlighted, or "flashing," to indicate a proximity to "backwalling" the vessel.

Figure 10:
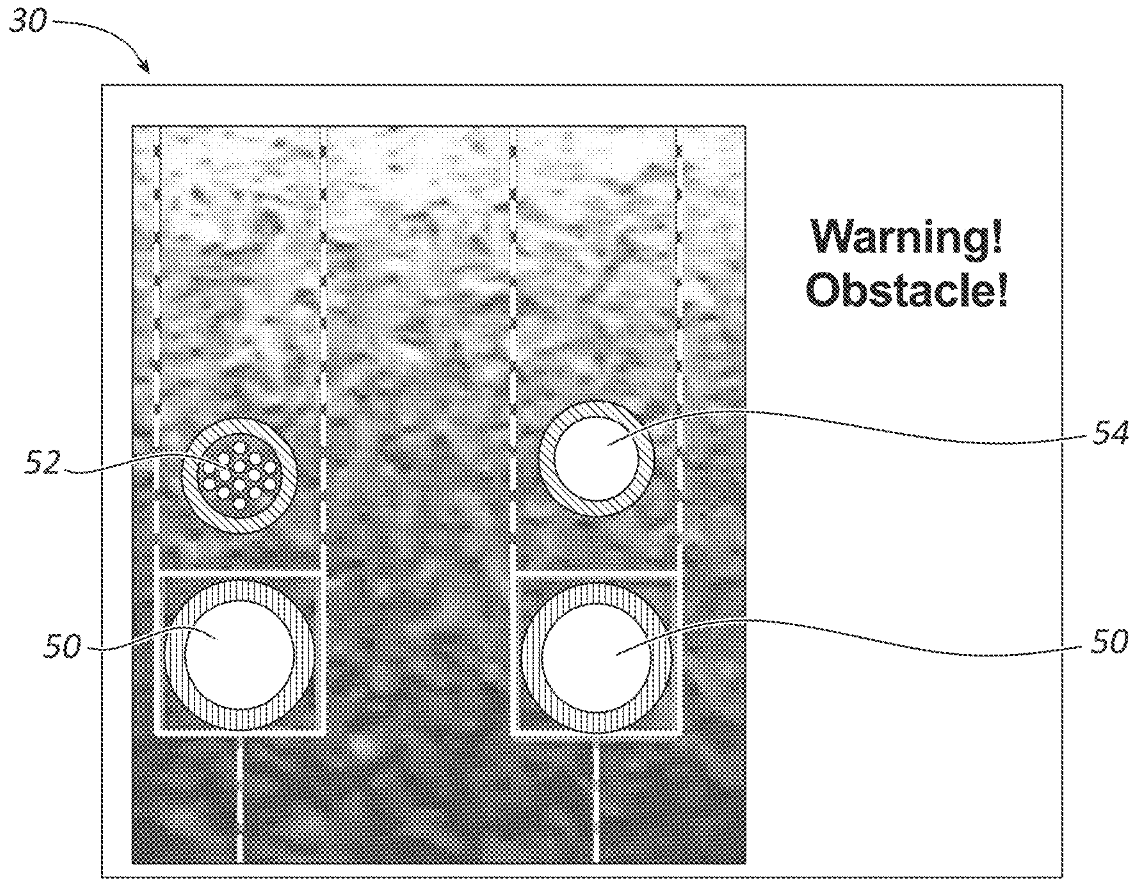
FIG. 10 illustrates an enhanced ultrasound image including iconography for potential obstructions between a medical device and a target blood vessel, in accordance with embodiments disclosed herein.

In an embodiment, as shown in FIG. 10, the system 10 can provide additional icons to identify potential obstructions between the target vessel 50 and the cannula 40. For example, a nerve bundle 52, or an arterial vessel 54, or the like, can be disposed between the target vessel 50 and the cannula 40. The system 10 can provide icons including different colors, patterns, labels, or the like, from that of icons highlighting the target vessels 50 to indicate to the clinician that an alternate path to the target vessel is required. The system 10 can further display additional visual, audible, or tactile alerts to notify the clinician of the obstruction.

Currently, determination of target vessels under ultrasound imaging is based on a subjective assessment by the clinician which can lead to sub-optimal vessels being accessed, failed access attempts, loss of vessel purchase leading to oedema, and other complications, and the like. However, advantageously, embodiments disclosed herein, or combinations thereof, can provide a clear, quantitative indication of suitable vessels to target prior to any insertion of the cannula. This prevents the clinician from accessing vessels only to find the vessel is too small to receive the cannula, too deep to provide sufficient vessel purchase, has sufficient flow and is the correct vessel type for the procedure. Further, embodiments can identify insertion trajectories and any potential obstructions and improve user handling of the imaging system.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A method of accessing a blood vessel, comprising:

utilizing an ultrasound system, the ultrasound system comprising:

an ultrasound probe; and a display communicatively coupled to at least one processor and the ultrasound probe;

depicting an ultrasound image sent from the ultrasound probe;

determining that motion of a target vessel depicted in the ultrasound image is caused solely by a positional instability of the ultrasound probe when the positional instability exceeds a threshold equated to normal bodily motion; and providing a first notification indicating the positional instability of the ultrasound probe.

2. The method according to claim 1, further comprising depicting an enhanced image of the ultrasound image, the enhanced image including an icon surrounding the target vessel.

3. The method according to claim 2, further comprising depicting the icon surrounding the target vessel in at least one of a color, a pattern, an intermittent feature, or an alphanumerical symbol to indicate an updated state.

4. The method according to claim 3, further comprising:

measuring a diameter of the target vessel and receiving a desired range of vessel occupancy; and indicating via the icon in the updated state whether a percentage vessel occupancy of the target vessel is within the desired range of vessel occupancy.

5. The method according to claim 1, wherein the ultrasound system includes a cannula, further comprising receiving updated information related to a dimension of the cannula.

6. The method according to claim 5, further comprising deriving the dimension of the cannula via the ultrasound system.

7. The method according to claim 6, wherein the dimension of the cannula includes one or both of a longitudinal length and a diameter.

8. The method according to claim 5, further comprising receiving updated information related to an angle of insertion of the cannula and a desired range of vessel purchase.

9. The method according to claim 8, further comprising predetermining the angle of insertion of the cannula.

10. The method according to claim 8, further comprising measuring the angle of insertion of the cannula using at least one of a needle guide or a permanent magnet and magnetic sensor array.

11. The method according to claim 5, further comprising providing a second notification indicating when a tip of the cannula is proximate a back wall of the target vessel.

12. The method according to claim 1, further comprising determining flow characteristics of the target vessel using Doppler measurements, pulsatile measurements, or a combination thereof.

13. The method according to claim 12, wherein determining the flow characteristics of the target vessel comprises determining a flow rate in the target vessel and assessing whether the target vessel is a vein or an artery based on the flow rate.

14. The method according to claim 1, further comprising measuring a change in a roundness of the target vessel and indicating a deviation of the roundness of the target vessel on the display.

15. The method according to claim 1, further comprising depicting an enhanced image of the ultrasound image including a guideline indicating a predicted trajectory of a cannula used in conjunction with the ultrasound system.

16. The method according to claim 15, wherein the guideline includes at least one of a first color or a first pattern to indicate when the predicted trajectory of the cannula intersects the target vessel and includes at least one of a second color or a second pattern to indicate when the predicted trajectory of the cannula does not intersect the target vessel.

17. The method according to claim 15, further comprising depicting an icon surrounding an obstruction disposed adjacent the predicted trajectory of the cannula between the cannula and the target vessel.

18. The method according to claim 17, wherein the icon includes at least one of a color, a pattern, an intermittent feature, or an alphanumerical symbol.

* * * * *